(12) United States Patent
Sopori

(10) Patent No.: US 7,238,912 B2
(45) Date of Patent: Jul. 3, 2007

(54) WAFER CHARACTERISTICS VIA REFLECTOMETRY AND WAFER PROCESSING APPARATUS AND METHOD

(75) Inventor: Bhushan L. Sopori, Denver, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 10/547,579

(22) PCT Filed: Oct. 6, 2004

(86) PCT No.: PCT/US2004/032899

§ 371 (c)(1),
(2), (4) Date: Aug. 31, 2005

(87) PCT Pub. No.: WO2005/036601

PCT Pub. Date: Apr. 21, 2005

(65) Prior Publication Data

US 2006/0219678 A1 Oct. 5, 2006

Related U.S. Application Data

(60) Provisional application No. 60/509,417, filed on Oct. 7, 2003.

(51) Int. Cl.
*B23K 26/38* (2006.01)
*B23K 26/12* (2006.01)
*H01L 21/00* (2006.01)
*G01N 21/47* (2006.01)

(52) U.S. Cl. .......................... 219/121.67; 219/121.72; 219/121.83; 219/121.86; 356/446; 438/463

(58) Field of Classification Search ........... 219/121.67, 219/121.68, 121.69, 121.72, 121.83, 121.84, 219/121.86; 356/236, 445, 446, 448; 438/463
See application file for complete search history.

(56) References Cited

U.S. PATENT DOCUMENTS

| | | | |
|---|---|---|---|
| 5,486,701 A | 1/1996 | Norton et al. |
| 5,517,315 A | 5/1996 | Small |
| 5,555,474 A | 9/1996 | Ledger |
| 5,564,830 A | 10/1996 | Bobel et al. |
| 5,581,346 A | 12/1996 | Sopori |
| 5,588,005 A | 12/1996 | Sheldon |
| 5,588,995 A | 12/1996 | Sheldon |
| 6,128,087 A | 10/2000 | Meredith, Jr. et al. |
| 6,275,295 B1 | 8/2001 | Sopori |

(Continued)

FOREIGN PATENT DOCUMENTS

FR 2698302 A 5/1994

(Continued)

*Primary Examiner*—Geoffrey S. Evans
(74) *Attorney, Agent, or Firm*—Paul J. White

(57) ABSTRACT

An exemplary system includes a measuring device to acquire non-contact thickness measurements of a wafer and a laser beam to cut the wafer at a rate based at least in part on one or more thicknesses measurements. An exemplary method includes illuminating a substrate with radiation, measuring at least some radiation reflected from the substrate, determining one or more cutting parameters based at least in part on the measured radiation and cutting the substrate using the one or more cutting parameters. Various other exemplary methods, devices, systems, etc., are also disclosed.

36 Claims, 25 Drawing Sheets

U.S. PATENT DOCUMENTS

| | | |
|---|---|---|
| 6,278,809 B1 | 8/2001 | Johnson et al. |
| 6,376,797 B1 | 4/2002 | Piwczyk et al. |
| 6,563,130 B2 * | 5/2003 | Dworkowski et al. ... 219/121.6 |
| 2002/0005958 A1 | 1/2002 | Sekiya |
| 2002/0039186 A1 | 4/2002 | Rosenberg |
| 2002/0167326 A1 | 11/2002 | Borden et al. |
| 2004/0150820 A1 * | 8/2004 | Nikoonahad et al. ....... 356/364 |
| 2004/0226926 A1 * | 11/2004 | Pollard .................. 219/121.84 |
| 2005/0236378 A1 * | 10/2005 | Boyle et al. ........... 219/121.67 |

FOREIGN PATENT DOCUMENTS

| | | |
|---|---|---|
| JP | 6-120334 A | 4/1994 |
| JP | 10-62129 A | 3/1998 |

* cited by examiner

EXEMPLARY REFLECTOMETER CHAMBER

EXEMPLARY ELEMENT

EXEMPLARY ELEMENT

EXEMPLARY SYSTEM

EXEMPLARY REFLECTOMETER

EXEMPLARY REFLECTOMETER

EXEMPLARY REFLECTOMETER

EXEMPLARY REFLECTOMETER

WAFER CHARACTERISTICS VIA REFLECTOMETRY AND WAFER PROCESSING APPARATUS AND METHOD

RELATED APPLICATIONS

This application claims the benefit of a U.S. Provisional Application having Ser. No. 60/509,417, entitled "Wafer Characteristics via Reflectometry and Wafer Processing Apparatus and Method", filed Oct. 7, 2003, which is incorporated by reference herein. This application is a continuation-in-part of a Patent Cooperation Treaty (PCT) Application having serial number PCT/US03/07804, entitled "Wafer Characteristics via Reflectometry", filed with the U.S. receiving office Feb. 14, 2003, which is incorporated by reference herein.

CONTRACTUAL ORIGIN OF THE INVENTION

The United States Government has rights in this invention pursuant to Contract No. DE-AC36-99GO10337 between the United States Department of Energy and the National Renewable Energy Laboratory, a Division of Midwest Research Institute.

TECHNICAL FIELD

The subject matter disclosed herein generally relates to reflectometry methods, devices and systems suitable for use in characterizing wafers and, in particular, to processing wafers.

BACKGROUND ART

Wafers find a variety of uses in the semiconductor, solar energy and other industries. Wafer quality often depends on variables such as thickness and surface characteristics. Depending on end use, poor quality wafers may have uneven thickness or uneven surface characteristics; whereas, higher quality wafers may have substantially uniform thickness and substantially uniform surface characteristics. In the semiconductor industry, where wafers are used as a substrate, wafer quality can crucially influence mechanical and/or electronic yield of wafer-based semiconductor circuits.

Wafer thickness can affect mechanical, electronic and optical behavior or performance. With respect to mechanical performance, increased thickness can minimize detrimental effects of fabrication or use associated stresses. With respect to electronic and optical performance, wafer thickness is often an important variable. Further, wafer thickness is often defined by distance between an upper wafer surface and a lower wafer surface. Characteristics of one or both of these surfaces generally affect electronic and optical performance.

Industries that rely on wafer-based technologies typically seek to control wafer thickness through any of a variety of conventional manufacturing and measurement techniques. In the semiconductor industry, wafer thickness may be controlled through various processing techniques that involve wafering (sawing), etching, and polishing, which typically produce flat wafers with substantially parallel surfaces. Thickness measurement of such wafers is fairly well defined and straightforward. For example, conventional measurement techniques include use of a dial gauge (e.g., a manual, mechanical measurement, generally used in the laboratory for a small number of wafers) and use of impedance (e.g., measurement of capacitance or eddy current loss in a radio frequency bridge configuration). Some conventional techniques, such as those that rely on impedance, can be implemented in a non-contact manner. For example, a coil may create an electromagnetic field proximate to a wafer, without actually contacting the wafer, and thereby generate one or more eddy currents in the wafer. Information related to the generated current or currents is then used to determine wafer thickness. Various impedance techniques can be quite rapid, on the order of a few seconds for each wafer, but they require knowledge of wafer properties such as resistivity. Further, impedance techniques are not well suited for determining or mapping variations in wafer thickness.

In general, the solar energy industry imposes certain demands on wafer quality. Such demands often need to be amenable to high throughput. For example, a typical manufacturing facility may process 50,000 wafers per day wherein a reasonable fraction of these wafers must be subject to measurement techniques to provide meaningful quality assurance. Concomitantly, such measurement techniques should be quite rapid. Other demands relate to wafer morphology, noting that wafers used in the solar energy industry are typically not flat. For example, silicon-based ribbons can exhibit surfaces that are substantially non-parallel with substantial variations in surface morphology. In such instances, an "average" thickness measurement and/or a thickness profile are useful. Yet other demands concerns crystallinity, i.e., the crystalline or multi- (or poly-) crystalline nature of wafers. Conventional impedance techniques can produce inaccuracies for multi- or poly-crystalline wafers because of extraneous impedance associated with grain boundaries and defects. Surface characteristics impose other demands because wafers used in the solar energy industry typically have some substantial degree of surface texture that acts to reduce surface reflectance and maximize optical absorption. Various aspects of surface texture can lead to inaccuracies in determination of thickness and/or surface characteristics. For example, surface roughness can be particularly detrimental for determinations based on optical measurement techniques.

Surface texture includes roughness and waviness, in addition, many surfaces have lay (e.g., directional striations across the surface). Roughness includes the finest (shortest spatial wavelength or spatial periodicity) irregularities of a surface. Roughness generally results from a particular production process or material condition. Waviness includes more widely spaced (longer spatial wavelength or spatial periodicity) deviations of a surface from its nominal shape. Waviness errors are intermediate in wavelength between roughness and form error. Note that the distinction between waviness and form error is not always made in practice, and it is not always clear how to make it. Lay refers to the predominant direction of the surface texture. Ordinarily lay is determined by the particular production process and geometry used. For example, turning, milling, drilling, grinding, and other cutting tool machining processes usually produce a surface that has lay: striations or peaks and valleys in the direction that the tool was drawn across the surface. Other processes produce surfaces with no characteristic direction: sand casting, peening, grit blasting, etc. Sometimes these surfaces are said to have a non-directional, particulate, or protuberant lay.

Clearly, the above demands are difficult to meet. The difficulties are further intensified by a need for minimizing the equipment and the measurement costs. The solar cell industry typically uses wafer weighing as a technique for monitoring wafer thickness while impedance-based techniques are often used to measure thickness of a very small number of total wafers in a single wafer production facility.

The solar energy industry has also identified a need to measure the spatial variations in wafer thickness. It has been observed that certain processes are affected by the local variations in the wafer thickness. For example, a process in solar cell fabrication involves firing a metal pattern to produce a low-resistivity contact. This process consists of screen printing a contact and spike-firing it at a temperature of about 800° C. in an infrared furnace. In this type of a furnace, the temperature acquired by a wafer depends on wafer thickness. Thus, a wafer that is thicker than the standard wafer (for which the process is optimized) will rise to a higher temperature. This can lead to the metal punching through a junction which will concomitantly degrade the open circuit photo-voltage (e.g., $V_{oc}$) and fill factor of the solar cell. On the other hand, a thinner wafer may not be sintered properly, resulting (again) in a low fill factor. Of course, similar behavior may occur within different regions of a wafer if wafer thickness is not uniform.

Thus, within the solar energy industry and other industries, a need exists for methods, devices and/or systems for measurement of and determination of wafer variables (e.g., mechanical properties, mechanical behavior, electrical properties, electrical behavior, optical properties, optical behavior, etc.). In particular, a need exists for methods, devices and/or systems that can yield meaningful results for wafers that may have substantial texture (e.g., roughness, etc.) and/or substantially non-parallel surfaces. Further, a need exists for rapid, accurate, and/or low-cost methods, devices and/or systems. Various exemplary methods, devices and methods disclosed herein address aforementioned needs and/or other needs.

BRIEF DESCRIPTION OF THE DRAWING

Features and advantages of the described implementations can be more readily understood by reference to the following description taken in conjunction with the accompanying drawings.

DISCLOSURE OF THE INVENTION

The following description includes the best mode presently contemplated for practicing various described implementations. This description is not to be taken in a limiting sense, but rather is made merely for the purpose of describing the general principles of the various implementations. The scope of the described implementations should be ascertained with reference to the issued claims.

Reflectance in an Exemplary Wafer

Various exemplary methods, devices and/or systems described herein rely on a total reflectance spectrum of a wafer. While a rigorous description of radiation at the boundary between two media (e.g., air and a wafer, etc.) or within a medium (e.g., a wafer, etc.) may be made using, for example, the Maxwell Equations, for purposes of brevity, a simplified approach is described with respect to FIG. 1.

Figure 1:
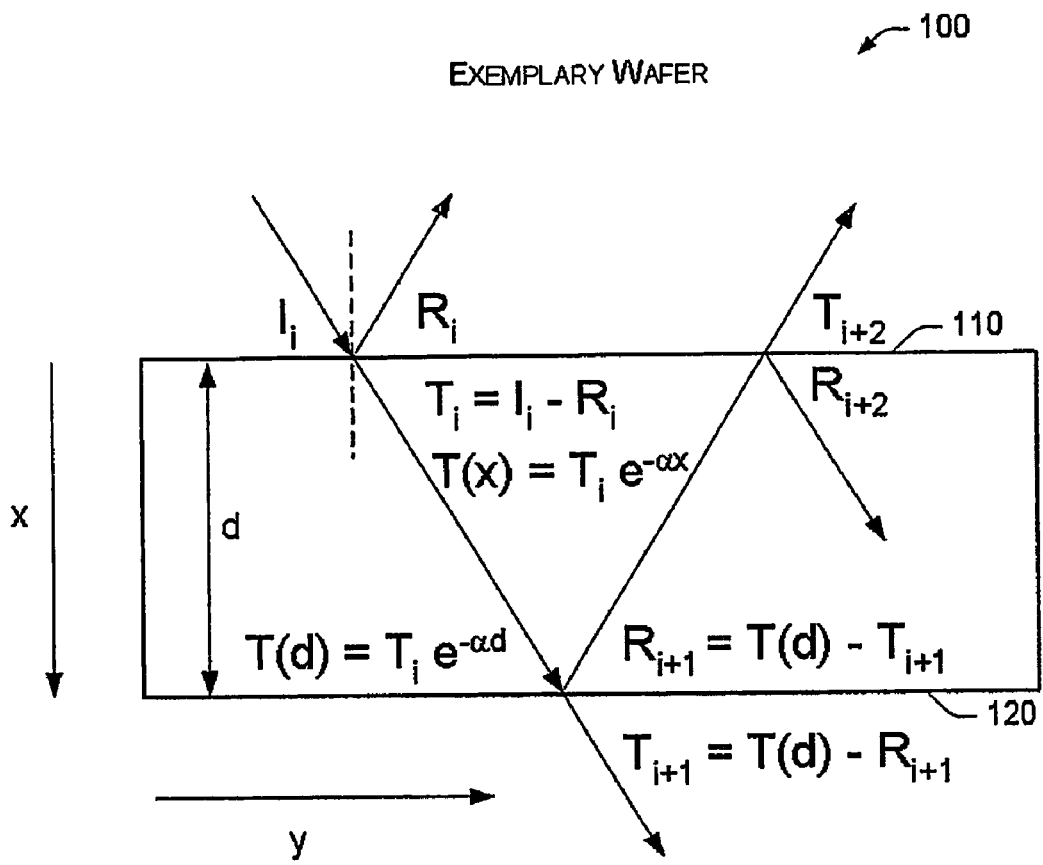
FIG. 1 is an illustration of an exemplary wafer showing incident radiation, reflected radiation and transmitted radiation.

FIG. 1 shows an exemplary wafer 100 having an upper surface 110 and a lower surface 120 which are substantially parallel and define a wafer thickness, d. Incident radiation, $I_i$, (e.g., electromagnetic radiation of a particular wavelength or wavelengths) illuminates the upper surface 110 wherein a portion of the incident radiation is reflected, $R_i$, and another portion is transmitted, $T_i=I_i-R_i$.

In general, radiation experiences a shift in phase and wavelength when traversing a boundary between dissimilar media. Further, radiation typically loses or transfers energy to a medium according to an absorption coefficient, $\alpha$, which is a material property of the medium. The process of energy absorption is approximated by the following equation (Equation 1) for a transmitted beam:

$$T(x) = T_i \exp(-\alpha x) \qquad (1),$$

where x is a dimension along the thickness, $T_i$ is an initial transmitted beam (e.g., corresponding to transmitted energy) and T(x) is a diminished transmitted beam (e.g., corresponding to a diminished energy) with respect to a distance x along the thickness. Absorption often depends on wavelength as well, for example, the absorption coefficient, $\alpha$, which may be approximated by $4\pi k x/\lambda$, where $\lambda$ is wavelength and k is the imaginary part of the optical constant of a medium and directly related to the absorption of a material (e.g., the extinction coefficient). Hence, shorter wavelength radiation typically absorbs more readily than longer wavelength radiation. Further, radiation having a very short wavelength will typically absorb almost entirely within a "skin depth" region at or near an incident boundary or surface.

According to Equation 1, at the lower surface 120, the transmitted energy has a value of $T(d)=T_i\exp(-\alpha d)$ due to absorption of radiation in the exemplary wafer 100. As for the upper surface 110, a boundary exists between the wafer 100 and another medium at the lower surface 120. Hence, radiation that reaches this boundary (e.g., the lower surface 120) will have a reflected portion, $R_{i+1}=T(d)-T_{i+1}$, and a transmitted portion, $T_{i+1}=T(d)-R_{i+1}$. Similarly, the reflected portion of the radiation, $R_{i+1}$, may eventually reach the boundary between the wafer 100 and another medium at the upper surface 110, wherein yet another portion $R_{i+2}$ will be reflected and yet another portion $T_{i+2}$ will be transmitted.

The exemplary wafer 100 demonstrates how wafer thickness as well as a wafer upper surface (e.g., the surface 110) and a wafer lower surface (e.g., the surface 120) may affect reflectance. While this example illustrates two internal reflections in an actual wafer, when illuminated by appropriated radiation, a wafer may experience thousands of internal reflections and hence emit thousands of transmitted portions. With respect to wavelength, incident radiation having a longer wavelength will typically result in more internal reflections and more transmitted portions than incident radiation having a shorter wavelength.

Total reflectance depends on reflectance, thickness and absorption according to the following equation (Equation 2):

$$R_T = R\left\{1 + \left[\frac{(1-R)^2 \cdot e^{-2\alpha d}}{1-R^2 \cdot e^{-2\alpha d}}\right]\right\}, \qquad (2)$$

where $$R = \frac{(n-1)^2 + k^2}{(n+1)^2 + k^2}$$

and n is the index of refraction.

Total transmittance also depends on reflectance, thickness and absorption according to the following equation (Equation 3):

$$T_T = \frac{(1-R)^2 \cdot e^{-2\alpha d}}{1-R^2 \cdot e^{-2\alpha d}}. \qquad (3)$$

As mentioned in the Background section, a wafer may have any of a variety of surface characteristics, including texture, roughness, waviness, lay (e.g., directional, arcuate, circular, radial, particulate, etc.), form or form error (e.g., typically larger scale errors), flaws (e.g., scratches, gauges, burrs, etc.), profile (e.g., line of intersection of a surface with a sectional plane), and others. Various exemplary methods, devices and/or systems disclosed herein are suitable for use in surface characteristic determinations for wafers.

Exemplary Methods for Wafer Thickness and/or Surface Characteristics

An exemplary method for determining wafer thickness and/or surface characteristics depends on information germane to total reflectance of a wafer. For example, an exemplary method includes receiving a signal that includes information germane to total reflectance of a wafer; comparing the information to information in a database (e.g., spectral information, etc.); and determining thickness and/or surface characteristics of the wafer based on the comparing.

To elaborate further, consider a measured reflectance signal or selected segments of a measured reflectance signal. Such a signal typically includes spectral information such as information germane to total reflectance of a wafer. For example, consider a signal that includes information about $R_i$ and $T_{i+2}$ as shown in FIG. 1. $R_i$ includes information about the upper surface 110 of the wafer 100 and $T_{i+2}$ includes information about the upper surface 110, the lower surface 120 and thickness of the wafer 100. Of course, the number of $T_{i+2}$ like contributions in a signal (e.g., $T_{i+4}$, $T_{i+6}$, $T_{i+8}$, etc.) will increase as the number of internal reflections in the wafer increases.

Once received, information in the signal may then be compared to information (e.g., spectral information for hypothetical wafers, etc.) in a database. In one example, the information in the database corresponds to calculated reflectance spectra for wafers of different thickness and/or surface characteristics. Three general scenarios may arise from this example wherein: (i) surface characteristics of the wafer are known; (ii) thickness of the wafer is known; and (iii) thickness and surface characteristics of the test wafer are unknown. In the first scenario, the known surface characteristics are used to narrow the comparing and more readily determine thickness of the wafer. In the second scenario, the known thickness of the wafer is used to narrow the comparing and more readily determine surface characteristics of the wafer. In the third scenario, the comparing performs a multivariable analysis to match the spectral information of the wafer with calculated spectral information for hypothetical wafers of various thickness and surface characteristics. The comparing may alternatively, or in addition to, compare to spectral information for actual wafers. Such comparisons may use any of a variety of interpolation techniques. Of course, other scenarios may arise, where some information is known a priori but not enough to forego an analysis to match thickness and/or surface characteristics.

While the aforementioned example uses information in a database, yet other examples may perform calculations to generate information and/or to analyze the information germane to total reflectance. For example, an exemplary method includes receiving a signal that includes information germane to total reflectance of a wafer; performing calculations to generate information (e.g., spectral information, etc.) and/or to analyze the information germane to total reflectance; and determining thickness and/or surface characteristics of the wafer based on the performing. Where calculations generate spectral information for hypothetical wafers, such information is optionally compared to the information germane to total reflectance.

Various exemplary methods may rely on software to perform calculations or to generate information (e.g., spectral information, etc.), which may be suitable for storage in a database. Commercially available software, such as, but not limited to, PV Optics optical modeling and design software for solar cells and modules (National Renewable Energy Laboratory, Division of U.S. Department of Energy) is suitable for performing such calculations. The PV Optics optical modeling and design software can generate information germane to light trapping of a solar cell or module, including multi-junction devices and any semiconductor material. For example, generated information ray indicate how much radiation is absorbed as well as how much of each wavelength of radiation is absorbed.

The PV Optics software can also account for textured surfaces common to most solar cells. The PV Optics software can analyze optical impact for very thin layers such as those associated with anti-reflection coatings or thin-film PV materials and reflective metal backings. In addition, PV Optics software can be used for other semiconductor devices such as optical detectors and certain types of display devices. The PV Optics software can also interface with optical processing instruments such as rapid thermal processing furnaces.

Regarding comparing database information or generated information to information germane to total reflectance, commercially available software for statistical analyses may be used. For example, various commercially available software packages allow for single and multivariable regression analyses. Such analyses are suitable for determining whether information germane to total reflectance of a wafer matches or fits database information or generated information. Further, such analyses may aid in determining thickness and/or surface characteristics of a wafer based on the comparing. For example, if the signal information for a wafer matches (e.g., within some bounds) certain information stored in a database (e.g., for a hypothetical or actual wafer) then a determination may be made as to the thickness and/or surface characteristics of the wafer.

Exemplary Device Capable of Implementing Methods

Figure 2:
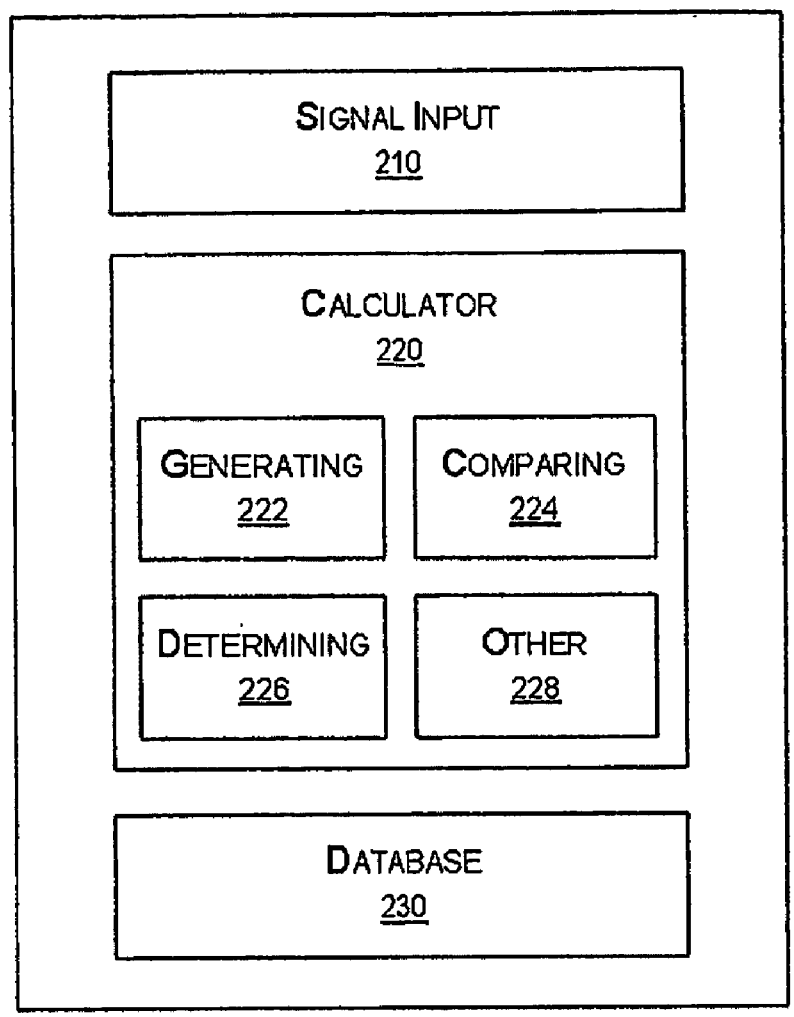
FIG. 2 is a block diagram of an exemplary device for determining wafer thickness and/or surface characteristics.

FIG. 2 shows a block diagram of an exemplary device 200 for implementing various exemplary methods. The device 200 includes a signal input block 210 for receiving a signal that includes information germane to total reflectance of a wafer. One or more appropriate signals may be received, for example, from a measurement unit (e.g., a reflectometer, etc.), an analysis unit (e.g., a computer, etc.), or a storage unit (e.g., database, disk drive, network, etc.). The device 200 further includes a calculator block 220 for performing various calculations. For example, the calculation block 220 optionally includes a generating block 222 for generating information, a comparing block 224 for comparing information, a determining block 226 for determining one or more characteristics (e.g., thickness, surface characteristics, etc.) of a wafer, and another block 228 that allows for other processes. The calculator block 220 is optionally programmable. Further, an exemplary device may rely on software, hardware or a combination of both to perform calculations and/or other functions. Where appropriate, the exemplary device 200 includes a database 230 for storing information.

Exemplary Methods and Reflectance or Wavelength Bounds

Some of the aforementioned exemplary methods and/or devices do not necessarily rely on associating spectral information with any particular reflectance bounds or wavelength bounds. However, as described herein, determinations for wafer thickness and/or surface characteristics are facilitated by acquiring, receiving, calculating and/or comparing spectral information within certain reflectance and/or wavelength bounds. Hence, various exemplary methods, devices and/or systems use one or more reflectance and/or wavelength bounds. Such bounds may define one or more regions, for example, in a plot of reflectance versus wavelength for a wafer various regions may exist that correspond to reflectance and/or wavelength bounds.

Polished Wafers

Figure 3:
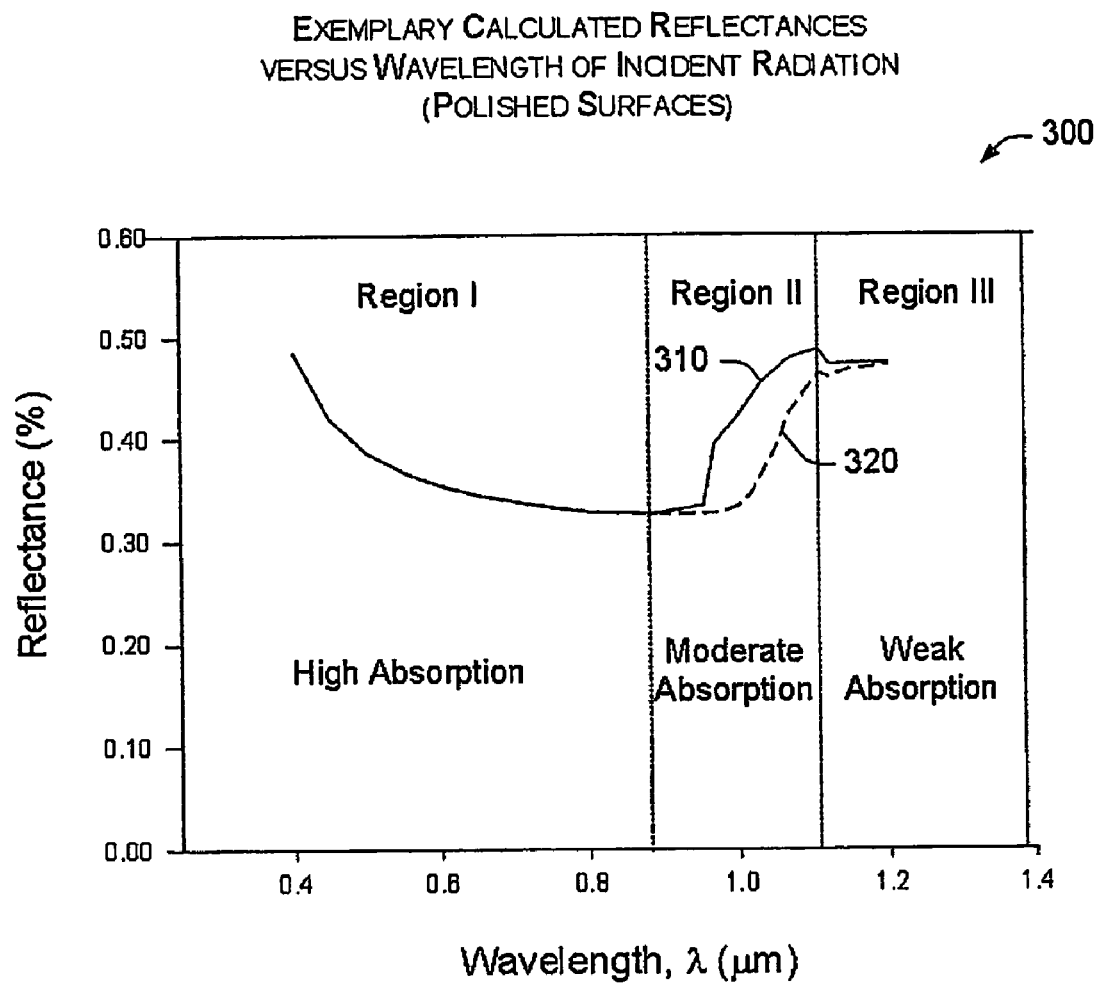
FIG. 3 is an exemplary plot of calculated reflectance (%) versus wavelength for two hypothetical wafers having polished surfaces and different thicknesses.

FIG. 3 shows an exemplary plot 300 of reflectance (%) versus wavelength, λ (μm), for two hypothetical wafers of different thickness. Calculated data 310 corresponds to a wafer having thickness of approximately 50 μm while calculated data 320 corresponds to a wafer having thickness of approximately 300 μm. In both instances, the wafers have a polished upper surface and a polished lower surface that are substantially parallel.

The plot 300 has three regions, labeled Region I, Region II and Region III. Region I corresponds to smaller wavelength radiation where high absorption occurs along with a high degree of reflection from the polished upper surface. In Region I, the reflectance diminishes substantially exponentially as a function of increasing wavelength (e.g., over the range from approximately 400 nm to approximately 900 nm). Further, in Region I, the calculated data for the 300 μm wafer 320 and the 50 μm wafer 310 exhibit no substantial differences. Hence, spectral information in Region I may provide little help in making thickness determinations. Again, in this example, the upper surfaces of each of the hypothetical wafers have identical characteristics.

Region II corresponds to moderate wavelengths where moderate absorption occurs. Moderate absorption allows for multiple internal reflections, which are effected by surface characteristics of both the upper surface and the lower surface of the wafers. In Region II, reflectance generally increases with increasing wavelength (e.g., over the range from approximately 900 nm to approximately 1100 nm) and a substantial difference exists between the calculated reflectance data for the 300 μm wafer 320 and the calculated reflectance data for the 50 μm wafer 310. Further, the reflectance for the 50 μm wafer is generally greater than the reflectance for the 300 μm wafer in Region II. Thus, in Region II reflectance generally decreases as a function of wafer thickness. Again, the absorption coefficient, α (e.g., where $\alpha = 4\pi k x/\lambda$), varies proportionally with respect to thickness and inversely with respect to wavelength. For the data in plot 300, k and λ are identical for both hypothetical wafers; thus, the absorption coefficient and data exhibit dependence of absorption coefficient and reflectance on thickness.

Region III corresponds to longer wavelengths wherein the absorption coefficient is even smaller than for Regions I or II. Hence, incident radiation in Region III absorbs weakly. Concomitantly, reflectance varies little for the two wafer thicknesses (e.g., 50 μm and 300 μm) when compared to Region II. Thus, imposition of reflectance and/or wavelength bounds corresponding to Region II can aid in determinations for wafer thickness.

In one instance, data are acquired only for wavelengths corresponding to a moderately absorbing region. In another instance, data are received only for wavelengths corresponding to a moderately absorbing region. In yet another instance, calculated data are calculated only for wavelengths corresponding to a moderately absorbing region. Another instance compares or analyzes only data for wavelengths corresponding to a moderately absorbing region. Of course, for these aforementioned instances, reflectances corresponding to a moderately absorbing region may be substituted for or used in addition to such wavelengths. Yet further, an exemplary method optionally uses a selected wavelength and/or a selected reflectance that correspond to a moderately absorbing region. These instances and/or associated exemplary methods may be referred to as using reflectance bounds and/or wavelength bounds.

Textured Wafers

Figure 4:
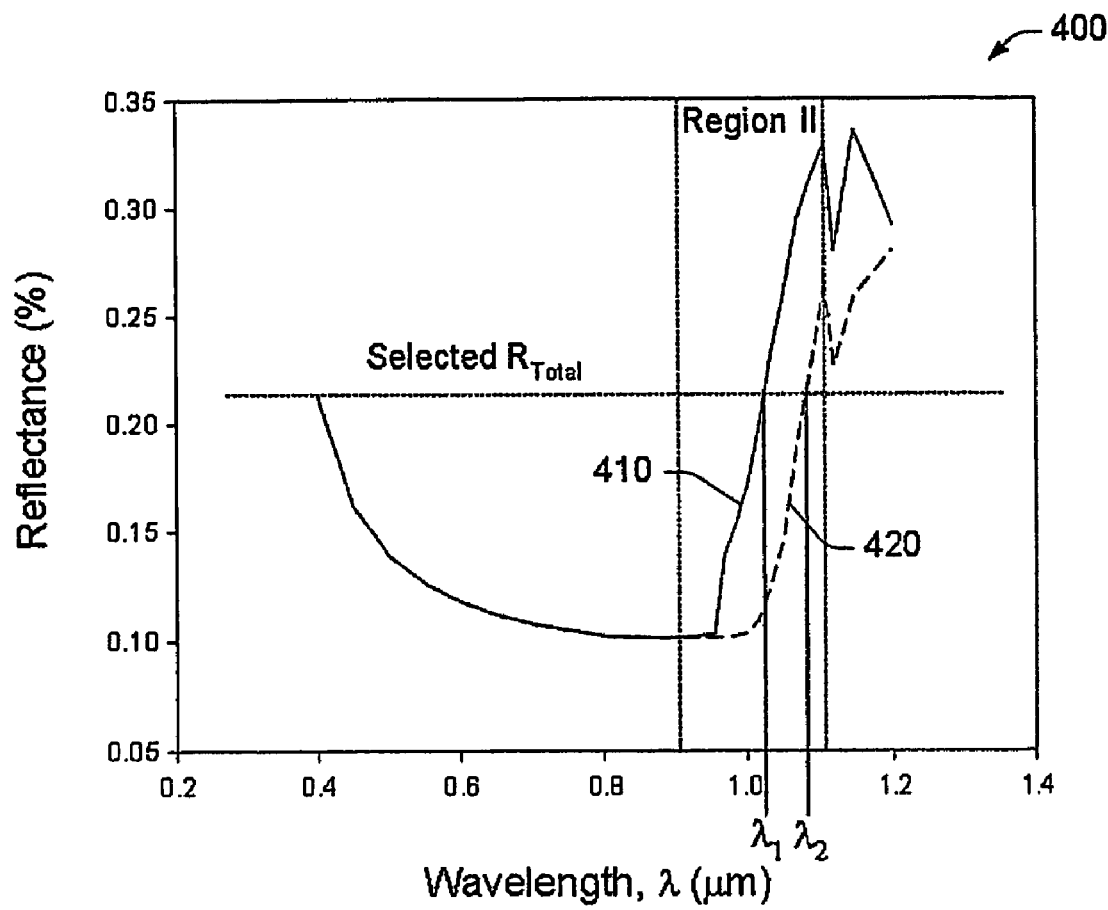
FIG. 4 is an exemplary plot of calculated reflectance (%) versus wavelength for two hypothetical wafers having substantial surface texture and different thicknesses.

FIG. 4 shows an exemplary plot 400 of reflectance (%) versus wavelength, λ (μm), for two hypothetical wafers of different thickness and having substantial surface texture (e.g., roughness or other characteristics representative of unpolished wafers). Calculated data 410 corresponds to a wafer having thickness of approximately 50 μm while calculated data 420 corresponds to a wafer having thickness of approximately 300 μm. In both instances, the wafers have an upper surface and a lower surface that are substantially parallel and have substantial surface texture.

The plot 400 includes three regions wherein Region II is shown. Calculated data 410, 420 exhibit the trends or dependencies described with respect to the calculated data of the hypothetical polished wafers 310, 320 of FIG. 3. However, the data presented in the plot 400 indicates that substantial surface texture can cause a decrease in total reflectance when compared to similar wafers having polished surfaces.

The plot 400 also includes a selected total reflectance, $R_T$, that corresponds to Region II, the region of moderate absorbance. The selected total reflectance intersects both reflectance curves 410, 420. The selected total reflectance intersects the thin wafer curve 410 at a wavelength $\lambda_1$ and intersects the thicker wafer curve 420 at a wavelength $\lambda_2$. In this example, $\lambda_1$ is less than $\lambda_2$ hence, for a selected total reflectance in a moderately absorbing region, wavelength increases with respect to wafer thickness. Note that the hypothetical wafers having polished surfaces exhibit this behavior as well.

An exemplary method includes selecting a total reflectance in a region where a wafer exhibits moderate absorbance and comparing a wavelength corresponding to the selected total reflectance to another wavelength. Further, the comparing may aid in determining thickness of the wafer.

Wafers on a Reflecting Support or having a Coated Surface

Figure 5:
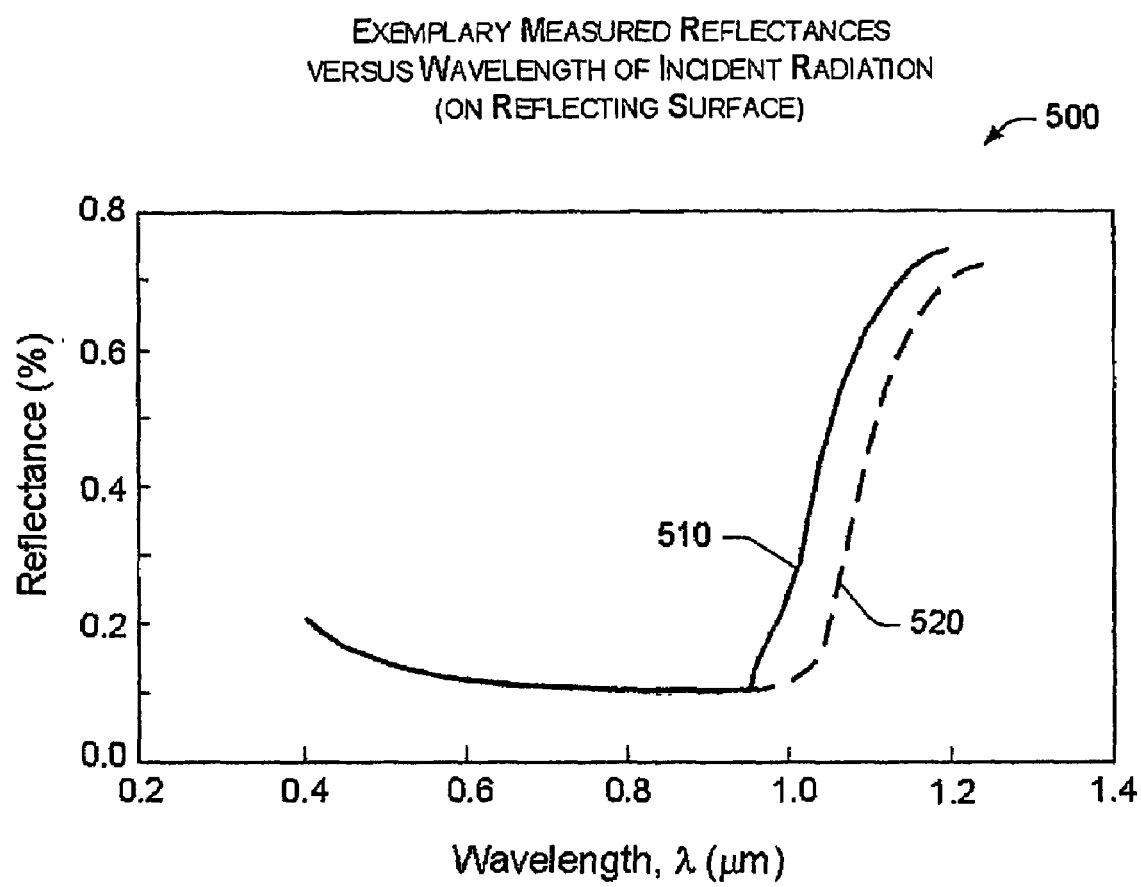
FIG. 5 is an exemplary plot of measured reflectance (%) versus wavelength for two wafers of different thickness positioned on a reflective support.

FIG. 5 shows an exemplary plot 500 of reflectance (%) versus wavelength, λ (μm), for two wafers of different thickness and having substantial surface texture (e.g., roughness or other characteristics representative of unpolished wafers) positioned on a reflecting support. Measured data 510 corresponds to a wafer having thickness of approximately 50 μm while measured data 520 corresponds to a wafer having thickness of approximately 300 μm. In both instances, the wafers have an upper surface and a lower surface that are substantially parallel and have substantial surface texture. Details of exemplary measurement techniques or methods are discussed further below.

In this example, use of a reflecting support extends the range or bounds of total reflectance in Region II. Of course, as an alternative to extend the range or bounds, a wafer's lower surface could be coated with a material that increases reflection at the lower surface (e.g., to create a significant impedance mismatch, difference in refractive indexes, etc.). This approach relies on use of reflectance and can enhance measurement sensitivity.

An exemplary method includes positioning a wafer on a reflecting support to extend the total reflectance in a moderately absorbing region, illuminating the wafer with radiation corresponding to the region and measuring reflectance of the wafer. Another exemplary method includes coating a surface of a wafer with a reflecting material to extend total reflectance in a moderately absorbing region, illuminating the wafer with radiation corresponding to the region and measuring reflectance of the wafer. In either of these exemplary methods, measured reflectances are optionally compared to other measured or calculated reflectances. Such a comparison can help in determining thickness of a wafer (e.g., actual or relative thickness).

Figure 6:
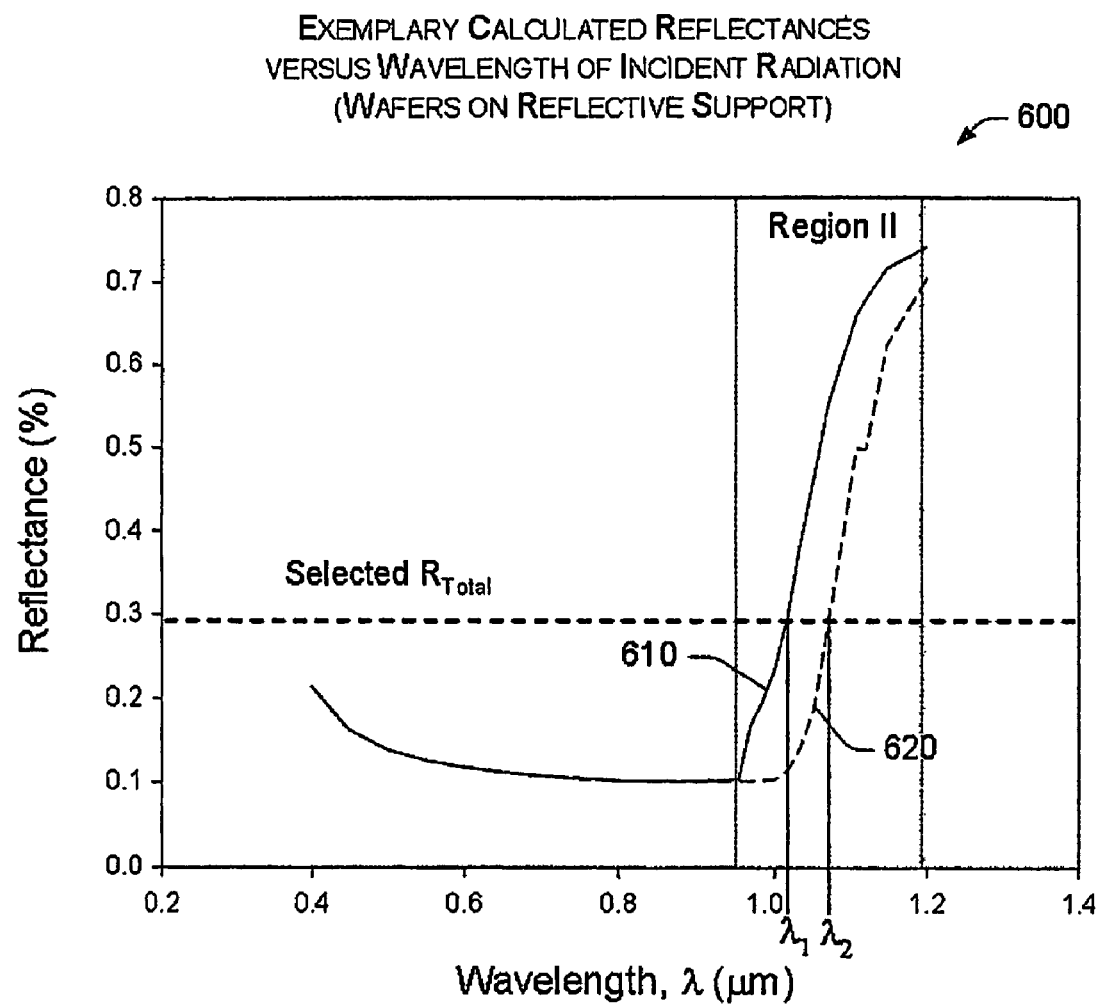
FIG. 6 is an exemplary plot of calculated reflectance (%) versus wavelength for two hypothetical wafers having different thickness and on a reflective support that further shows a selected total reflectance and corresponding wavelengths.

FIG. 6 shows an exemplary plot 600 of reflectance (%) versus wavelength, λ (μm), for two hypothetical wafers of different thickness and having substantial surface texture (e.g., roughness or other characteristics representative of unpolished wafers) positioned on a reflecting support. Calculated data 610 corresponds to a wafer having thickness of approximately 50 μm while measured data 620 corresponds to a wafer having thickness of approximately 300 μm. In both instances, the wafers have an upper surface and a lower surface that are substantially parallel and have substantial surface texture. Further, the reflecting support has properties of an aluminum reflector suitable for use in a reflectometer.

The calculated data presented in the plot 600 are suitable for use in comparing measured and calculated reflectances, which, in turn, can help in determining thickness of a wafer. For example, the plot 600 shows a selected total reflectance, $R_T$, and corresponding wavelengths $\lambda_1$ and $\lambda_2$. In this example, the total reflectance is approximately 0.3%, $\lambda_1$ is approximately 1.05 μm and $\lambda_2$ is approximately 1.3 μm. Such information may be used in, for example, a comparison with data presented in plot 500 of FIG. 5.

Figure 7:
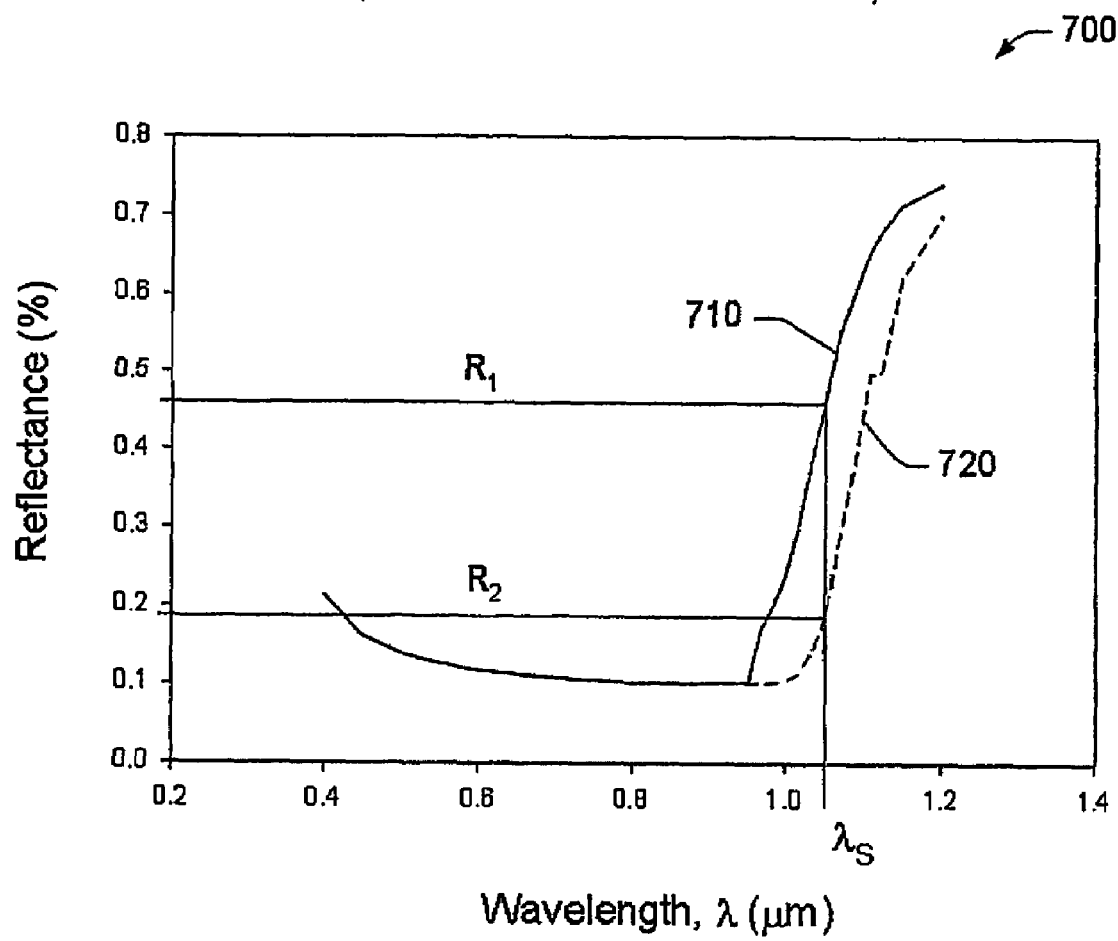
FIG. 7 is an exemplary plot of calculated reflectance (%) versus wavelength for two hypothetical wafers having different thickness and on a reflective support that further shows a selected wavelength and corresponding reflectances.

FIG. 7 shows a plot 700 that includes the calculated data of the plot 600. However, in the plot 700, a wavelength, $\lambda_S$, is selected to yield a first corresponding reflectance, $R_1$, for a first wafer and a second corresponding reflectance, $R_2$, for a second wafer. In general, the wavelength, $\lambda_S$, is selected to lie within a moderately absorbing region.

An exemplary method includes selecting a wavelength in a moderately absorbing region, measuring and/or calculating a corresponding reflectance for a wafer (e.g., actual or hypothetical) illuminated by radiation at the wavelength. According to this exemplary method, the reflectance is optionally used for comparing reflectances and/or determining thickness of a wafer.

Another exemplary method includes selecting a wavelength in a moderately absorbing region, illuminating a wafer with radiation and then interposing a suitable narrowband filter that allows for transmission of radiation having the selected wavelength from the wafer to a radiation detector. Of course, a band of wavelengths (e.g., wavelengths within some bounds) may be selected wherein the band lies substantially within a moderately absorbing region. In general, signal amplitude (e.g., intensity) of the radiation transmitted through such a filter is inversely related to wafer thickness. Hence, under such circumstances, an increase in detected amplitude (e.g., intensity) corresponds to a decrease in wafer thickness. As described further below, such an exemplary method may aid in imaging wafer thickness.

Exemplary Wafers with and without Reflecting Support

Figure 8:
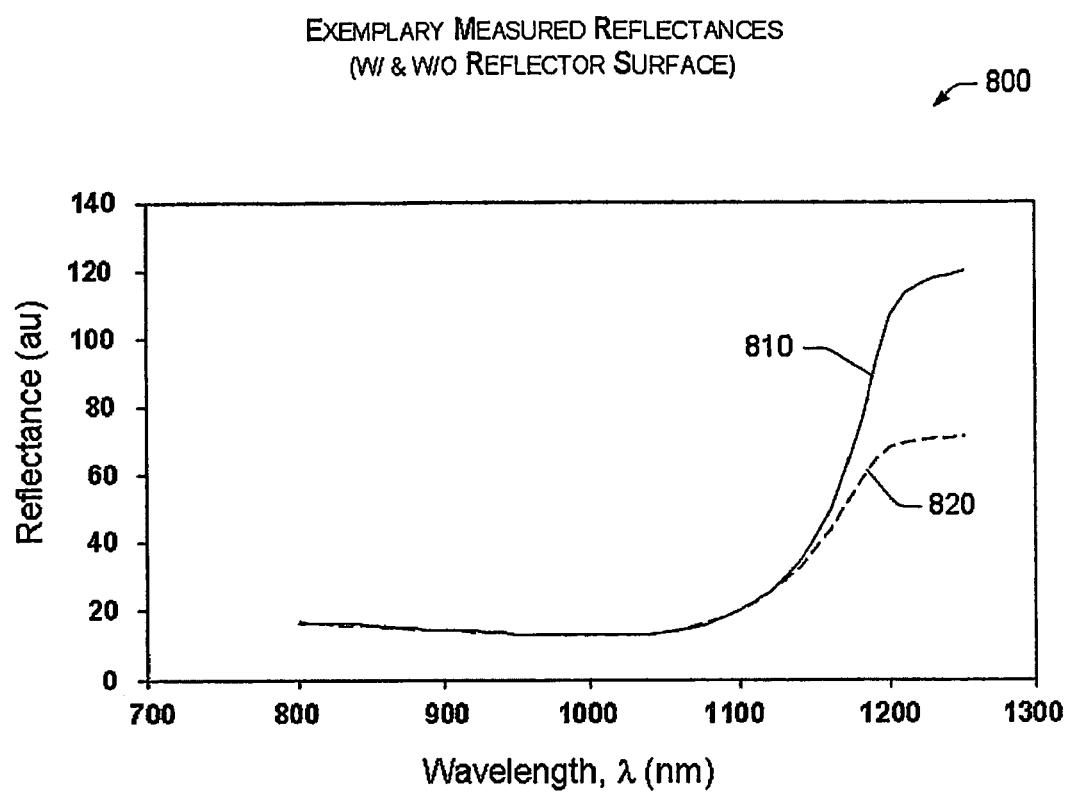
FIG. 8 is an exemplary plot of measured reflectance (au) versus wavelength for a wafer on a reflective support and a wafer on a substantially non-reflective support.

FIG. 8 shows a plot 800 of measured data for wafers with a reflecting surface 810 and without a reflecting surface 820. The data, plotted as reflectance (au) versus wavelength (nm), exhibits extension of reflectance in a moderately absorbing region through use of a reflecting support (or surface). In this example, the wafer is a commercially available double side textured (DST), crystalline Si wafer (c—Si).

Figure 9:
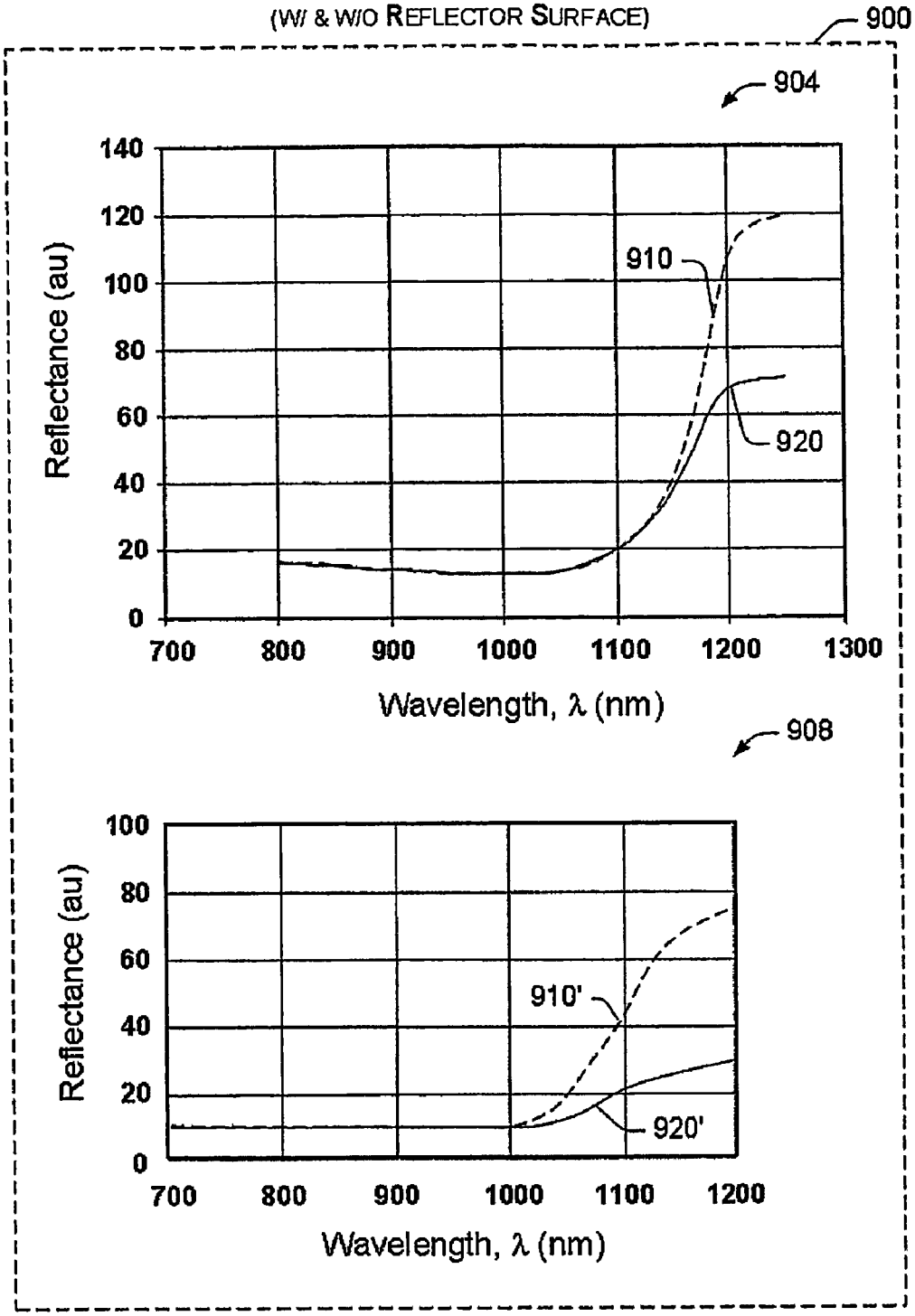
FIG. 9 is a comparison of an exemplary plot of measured reflectance versus wavelength and an exemplary plot of calculated reflectance versus wavelength.

FIG. 9 shows a comparison of plotted data 900 that includes a plot 904 of measured data and a plot 908 of calculated data for wafers with a reflecting surface 910, 910' and without a reflecting surface 920, 920'. The data, plotted as reflectance (au) versus wavelength (nm), exhibits extension of reflectance in a moderately absorbing region through use of a reflecting support (or surface). While differences exist between the measured and calculated data, both sets of data exhibit a significant extension of reflectance in a moderately absorbing region.

An exemplary method includes measuring reflectance of a wafer on a first support and measuring reflectance of the wafer on a second support wherein the supports have different reflecting properties. For example, the first support may have a substantially non-reflecting surface and the second support may have a substantially reflecting surface. Such reflectance data may be subsequently compared (e.g., to measured or calculated data) or otherwise analyzed to aid in determining wafer thickness and/or surface characteristics. A particular implementation of such an exemplary method includes positioning a wafer on a support having controllable reflecting properties (e.g., liquid crystal, etc.) or on a substantially transparent support (or in a holder) wherein an underlying layer has controllable reflecting properties. Of course, more than two supports, reflecting properties, etc., may be used. For example, a liquid crystalline surface may allow for a range of reflecting properties wherein continuous measurement of reflectance of a wafer occurs as the reflecting properties are varied over the range. A resulting curve of reflectance for the wafer versus reflecting properties (e.g., for one or more wavelengths) can aid in determining wafer thickness and/or surface characteristics. An exemplary controller optionally controls a reflecting support as well as a reflectometer (see, e.g., reflectometers described below, etc.) and/or a processing device (e.g., the device 200, etc.).

Exemplary Wafers Having Various Surface Characteristics

Figure 10:
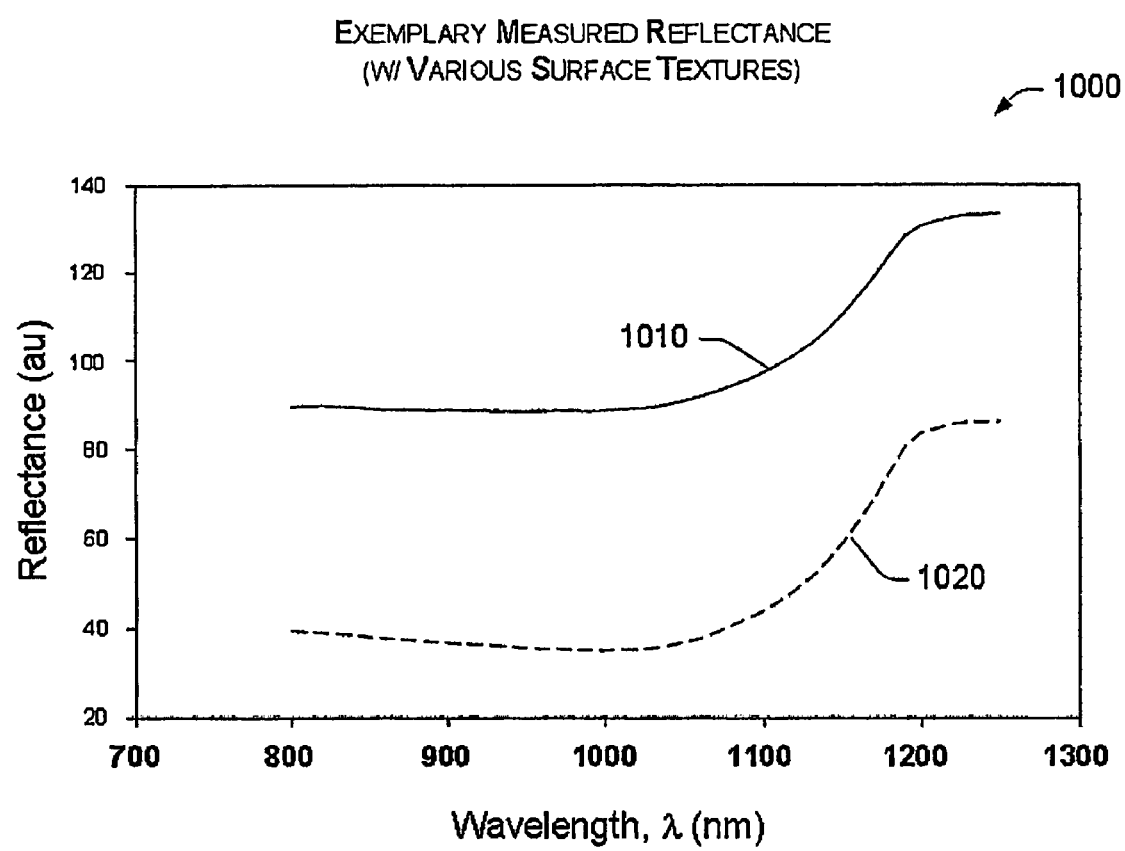
FIG. 10 is an exemplary plot of measured reflectance (au) versus wavelength for a wafer having a polished upper surface and a lower surface with substantial surface texture and another wafer having a polished lower surface and an upper surface with substantial surface texture.

FIG. 10 shows a plot 1000 of measured reflectance data for a first wafer 1010 having a polished upper surface and a lower surface with substantial texture and measured reflectance data for a second wafer 1020 having an upper surface with substantial texture and a polished lower surface. In this example, the wafers were commercially available multicrystalline Si wafers (mc—Si) with substantially equal thickness. Data in the plot 1000 indicate that reflectance varies with respect to surface characteristics. Further, variations in reflectance exist over a wide range of wavelengths, including wavelengths typically less than and/or typically greater than those associated with moderate absorption. An exemplary method includes measuring reflectance of a wafer at one or more wavelengths and comparing or otherwise analyzing the measured reflectance to determine one or more surface characteristics of the wafer.

Figure 11:
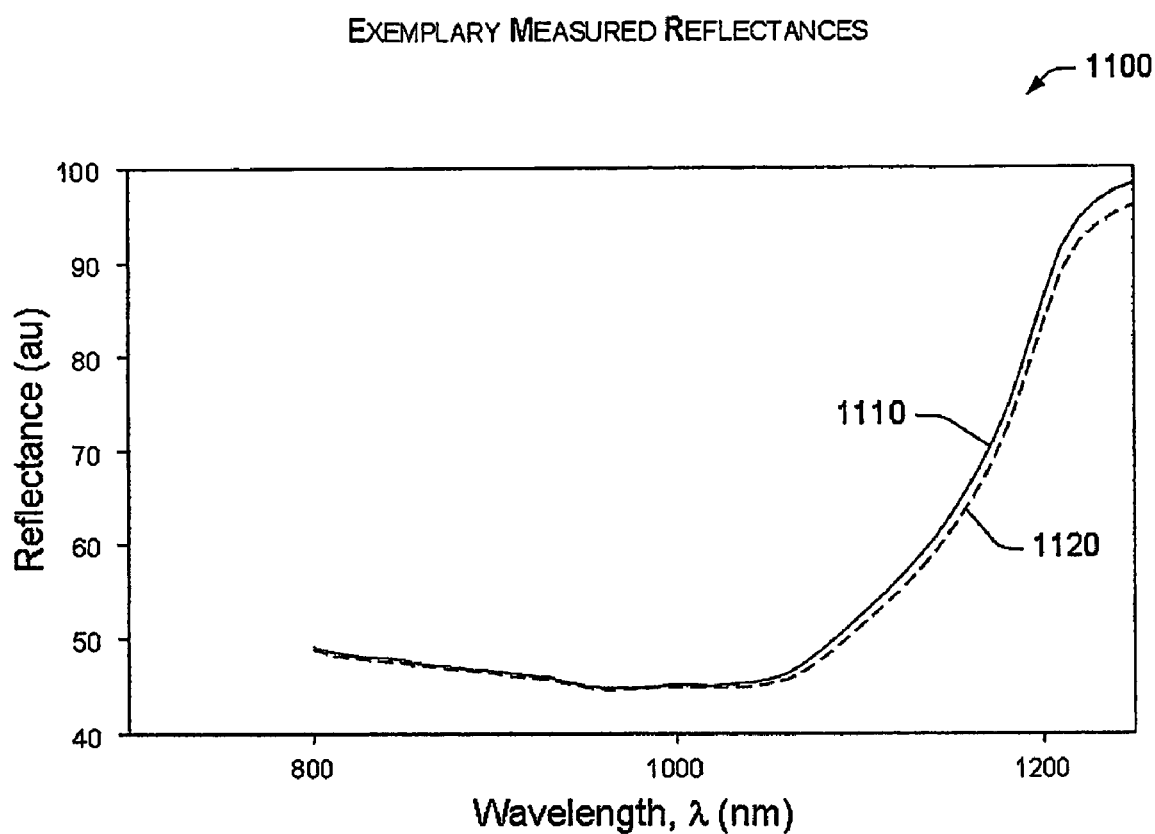
FIG. 11 is an exemplary plot of measured reflectance versus wavelength for two wafers having different thickness and/or surface characteristics.

FIG. 11 shows a plot 1100 of measured reflectance data for a first wafer 1110 and measured reflectance data for a second wafer 1120. In this example, the wafers were commercially available mc-Si wafers (approximately 125 mm by 125 mm) having front texture (FT, e.g., upper side texture) and back polished (BP, e.g., lower side polished), each wafer having about a 50 µm bow and an original wafer thickness of approximately 300 µm. Data in the plot 1100 indicate that the first wafer has a thickness less than that of the second wafer, in particular, the first wafer is approximately 20 µm thinner than the second wafer. In this example, one of the wafers was processed using a polishing technique to decrease its thickness by approximately 20 µm. An exemplary method includes determining wafer thickness or a difference in wafer thickness to a resolution equal to or greater than approximately 20 µm.

Various exemplary methods can use measured data that inherently average a wafer or thickness of a wafer. For example, an exemplary method may illuminate an entire wafer and then measure or detect radiation reflected or emitted from the entire wafer. In this example, the measured or detected radiation represents an average and where such a measured or detected value is used to determine thickness, the thickness represents an average thickness of the wafer. The solar energy industry uses any of a variety of different types of wafers, including ribbon wafers. In general, ribbon wafer do not have substantially parallel upper and lower surfaces (e.g., they may be considered non-planar) but rather have a taper that tapers away from the middle of the ribbon wafer. Average thickness is typically a suitable measure for such ribbon wafers and can aid in crystal growth processes or processing.

Mapping or Imaging Wafers

Various exemplary methods described herein are suitable for creating spatial maps or images of wafer thickness. For example, where a narrow-band filter is interposed between a wafer and a CCD array (e.g., a matrix of individual sensing elements) placed at or near the focal plane of an optical imaging setup for the wafer, the two dimensional optical image will vary with respect to local wafer thickness (e.g., wherein each element senses a radiation intensity that corresponds to an image pixel). Thus, such an image may be considered a quasi-three dimensional wafer image. As mentioned, intensity typically varies inversely to thickness; thus, in such an instance, low local intensity corresponds to a greater thickness and a high local intensity corresponds to a lesser thickness. Again, such a relationship between reflectance and thickness can exist in a moderately absorbing region.

Of course, an exemplary device (e.g., the device 200, etc.) may aid in relating thickness and radiation intensity. While CCD arrays are commonly used as image sensors, other image sensors may also be suitable, including, but not limited to, radiation sensitive film.

Exemplary Reflectometers

Various exemplary methods described herein optionally use a reflectometer (e.g., a reciprocal reflectometer such as a Sopori reflectometer, a PV reflectometer or a GT reflectometer, etc.) to measure or acquire spectral information germane to thickness and/or surface characteristics of a wafer. In general, a reciprocal reflectometer can measure a reflectance spectrum of a wafer in less than approximately 100 ms. Associated reflectometer equipment (e.g., computer, controller, etc.) can deconvolve an acquired reflectance spectrum to separate parameters that relate to various characteristics of a wafer.

Figure 12:
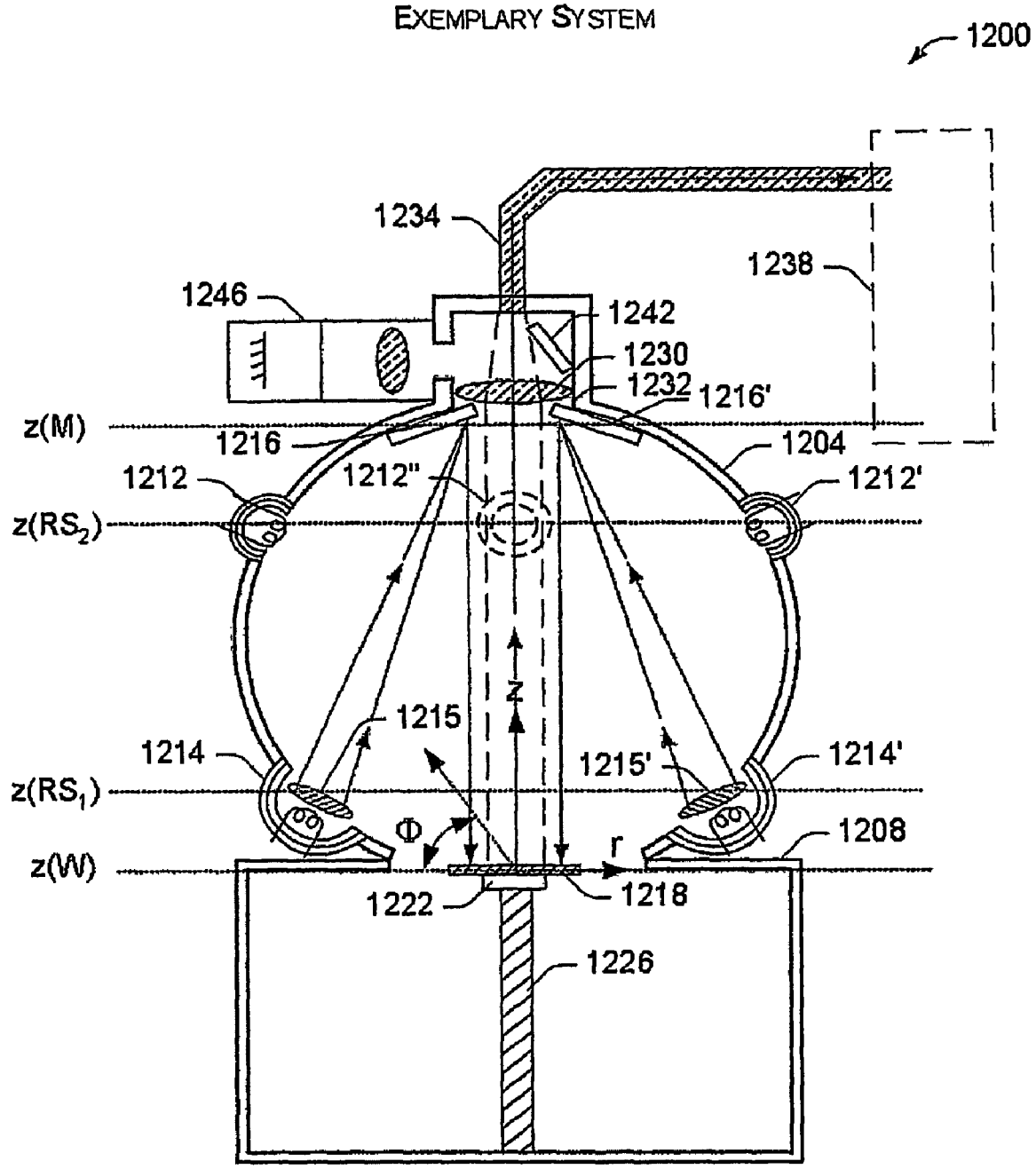
FIG. 12 is a cross-sectional view diagram of an exemplary system that includes a reflectometer.

FIG. 12 shows a cross-sectional view of an exemplary reflectometer system 1200. Various features of such a system were disclosed in U.S. Pat. No. 6,275,295, to Sopori, issued Aug. 14, 2001, which is incorporated herein by reference. With respect to the system 1200, the description herein discloses additional and/or alternative features. The reflectometer of the system 1200, as shown in cross-section (e.g., across an azimuthal angle, θ in substantially hemispherical coordinates), includes an axial dimension, z, a radial dimension r and an altitudinal dimension Φ (e.g., an altitudinal angle). The system 1200 includes a substantially spherical chamber 1204 centered on a z-axis (e.g., r=0) and operatively coupled at a lower end (e.g., approximately the horizon) to a radiation baffle 1208. The chamber 1204 is a partially walled chamber as it may include one or more openings. As described herein, a chamber is generally a walled chamber wherein one or more walls define the chamber space. Further, in most instances, the chamber is a partially walled chamber where the defining wall, or walls, may include one or more openings such as an aperture, etc.

In general, a wafer is positioned substantially on the horizon (e.g., z=0) and substantially centered (e.g., center of wafer at approximately r=0). The chamber 1204 includes a plurality of radiation sources 1212, 1212', 1212" arranged at an altitudinal angle (e.g., Φ approximately 60°) at a distance (e.g., z=z($RS_2$)) along the z-axis. This particular example includes four radiation sources (referred to collectively as $RS_2$) wherein the fourth (i.e., a fore source) is not shown.

The system 1200 includes additional radiation sources 1214, 1214' (referred to collectively as $RS_1$) arranged at a lesser altitudinal angle (e.g., Φ approximately 10°) and at a lower distance along the z-axis (e.g., z=z($RS_1$)). These additional radiation sources 1214, 1214' further optionally have associated optical elements 1215, 1215' (e.g., lenses, etc.) to direct radiation at one or more reflective surfaces 1216, 1216' (e.g., mirrors, prisms, etc.), which are located at a relatively large altitudinal angle (e.g., Φ approximately 80°, etc.) and at a relatively high distance along the z-axis (e.g, z=z(M)). In this exemplary system 1200, the radiation sources 1214, 1214' ($RS_1$) rely on the optical elements 1215, 1215' to direct radiation from the sources to the one or more reflective surfaces 1216, 1216'. In turn, the one or more reflective surfaces 1216, 1216' direct radiation to a wafer 1218, which is positioned at or near the base of the chamber 1204 (e.g., z=z(W) and centered at approximately r=0).

The system 1200 essentially functions by illuminating the wafer 1218 using any or all of the radiation sources (e.g., $RS_1$, $RS_2$). In this example, the wafer 1218 lies on a support or platform 1222 attached to an end of a post 1226 positioned within the baffle 1208. Once illuminated, the wafer 1218 reflects radiation toward an opposing end of the chamber 1204 (e.g., substantially normal to an upper surface of the wafer 1218). The opposing end of the chamber 1204 optionally includes an optical element 1230 (e.g., a lens, etc.), set in an upper aperture 1232, that directs the reflected radiation to a collector 1234 (e.g., an optical fiber, a light pipe, etc.). The optical element 1230 may be adjustable and part of an optical system for measurement (e.g., directing radiation to a detector, etc.) and/or imaging (e.g., having an associated focal length, etc.). The collector 1234 provides a path to a detector or analyzer 1238 for detecting or analyzing the reflected radiation. According to the description herein, the detector or analyzer 1238 optionally includes features or components of the exemplary device 200 of FIG. 2. The exemplary system 1200 may measure reflectance of a wafer as a function of wavelength.

The exemplary system 1200 also includes yet another optical element 1242 (e.g., a semi-transparent mirror, a lens, a prism, etc.) that can direct reflected radiation to another unit 1246 (e.g., an imaging unit, a camera, etc.). The optical element 1242 optionally allows for radiation to reach the collector 1234 and to reach the unit 1246 (e.g., a prism or semi-transparent mirror). Alternatively, a mechanism exists to select either the collector 1234 or the unit 1246 (e.g., a mechanism capable of activating or positioning the optical element 1242). An exemplary element and an associated exemplary mechanism for directing radiation are described further below.

In general, the chamber 1204 has a highly absorbing inner surface that reduces radiation scatter within the chamber 1204, which, in turn, can enhance signal to noise ratio of radiation reflected (e.g., externally or internally) in a direction substantially normal to the wafer 1218 (e.g., along the z-axis). For example, the one or more walls that define the chamber may include a highly absorbing inner surface. The exemplary system 1200 may achieve a signal to noise ratio of approximately 200.

Wafer Illumination and Surface Characteristics

As already mentioned and exhibited in the plot 1000 of FIG. 10, surface characteristics of a wafer affect reflectance. In general, wafers having substantial surface texture (e.g., roughness, etc.) reflect radiation in a more diffuse manner than wafers having one or more substantially polished surfaces. The exemplary system 1200 can measure reflectance for wafers having substantial surface texture. In particular, the exemplary system 1200 can perform such measurements using radiation sources positioned at altitudinal angles (e.g., Φ) that are substantially less than 90° (e.g., positioned well off the z-axis or zenith and not substantially normal to a wafer). Such radiation sources (e.g., $RS_2$) direct radiation in a manner that can illuminate a variety of surface features (e.g., consider a wafer having a jagged profile).

The exemplary system 1200 can also use such radiation sources (e.g., $RS_2$) to measure reflectance for wafer having less surface texture, for example, wafers having one or more polished surfaces, particularly an upper polished surface and/or wherein the upper surface is substantially normal to the rz-plane (e.g., substantially parallel to the rΘ-plane). However, reflectance measurements for such wafers may be enhanced through use of radiation that illuminates a wafer from a direction substantially normal to the wafer. The radiation sources $RS_1$ of the system 1200 can allow for such illumination. Again, the radiation sources 1214, 1214' ($RS_1$) have associated optical elements 1215, 1215' and reflecting surfaces 1216, 1216' that can direct radiation normal to a wafer.

Figure 13:
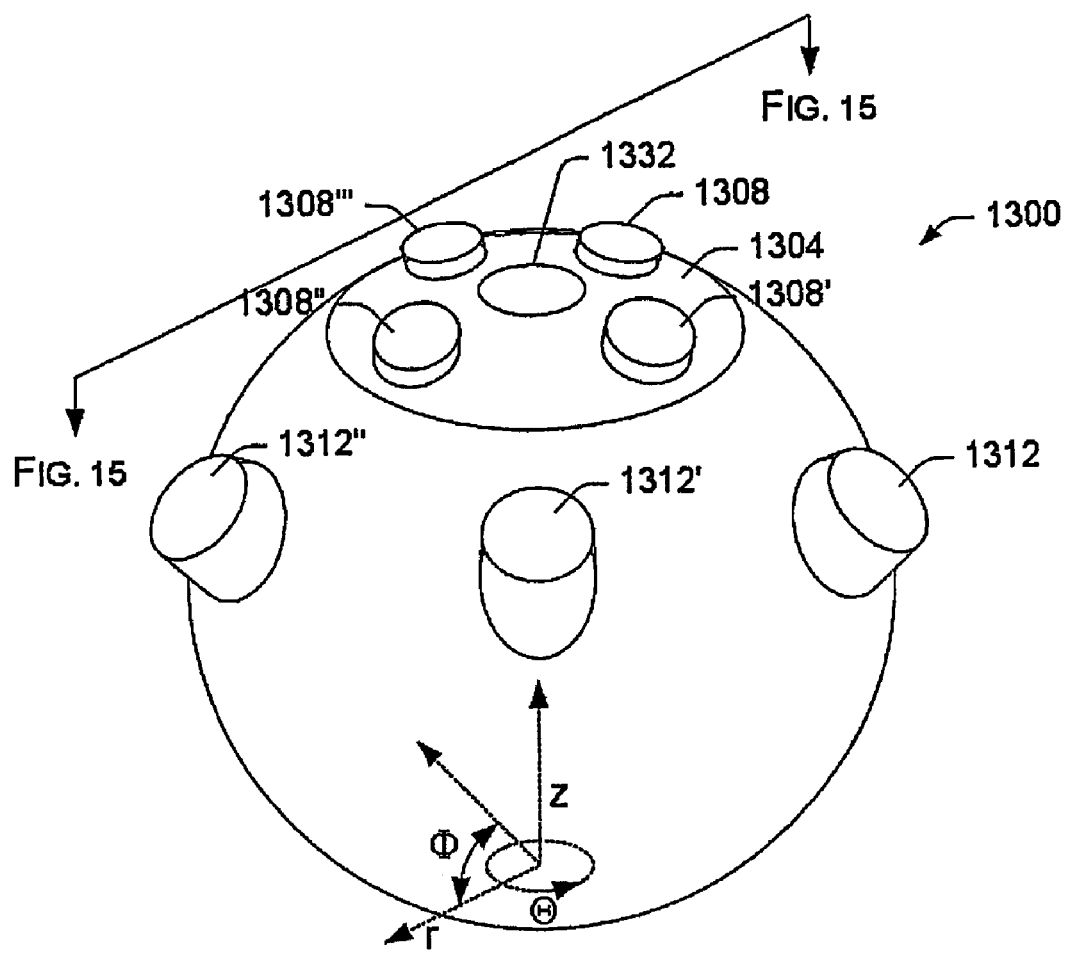
FIG. 13 is a perspective view diagram of an exemplary reflectometer chamber.

FIG. 13 shows another exemplary chamber 1300 having another exemplary arrangement of radiation sources. The exemplary chamber 1300 includes an upper section 1304 that has a plurality of radiation sources 1308, 1308', 1308", 1308''' positioned thereon, referred to herein as $RS_3$ (e.g., being positioned the furthest distance from a wafer along the z-axis: z($RS_3$)>z($RS_2$)>z($RS_1$)). The plurality of radiation sources $RS_3$ are positioned substantially normal to the rΘ-plane (where Θ is the azimuthal angle), for example, at an altitudinal angle Φ equal to or greater than approximately 70°. These radiation sources are suitable for illuminating a wafer with radiation directed substantially normal to the wafer. While the exemplary chamber 1300 has four radiation sources 1308, 1308', 1308", 1308''', a lesser or greater number are optionally used. For example, an exemplary chamber optionally includes a single ring-shaped source positioned at or near an upper aperture 1332, two sources positioned at altitudinal angles (e.g., Φ) equal to or greater than approximately 70°, or 8 sources positioned at altitudinal angles (e.g., Φ) equal to or greater than approximately 70°, etc.

The exemplary chamber 1300 optionally includes additional radiation sources 1312, 1312', 1312", etc., positioned at lesser altitudinal angles (e.g., Φ), referred to as $RS_2$. For example, such additional radiation sources may be positioned at altitudinal angles less than approximately 70°. In general, such additional radiation sources may be positioned at altitudinal angles equal to or greater than approximately 30° and less than approximately 70°. These additional sources $RS_2$ are suitable for illuminating wafers having substantial surface texture (e.g., roughness). Hence, the exemplary chamber 1300, as shown, is suitable for illuminating wafers having a wide variety of surface characteristics. A controller, such as the controller 1238, optionally controls radiation sources and may select or adjust illuminating radiation to account for such surface characteristic variations. For example, a controller may provide power to a plurality of radiation sources in a manner that allows for essentially rotational illumination (e.g., sequential illumination at an angular frequency, etc.).

Figure 14:
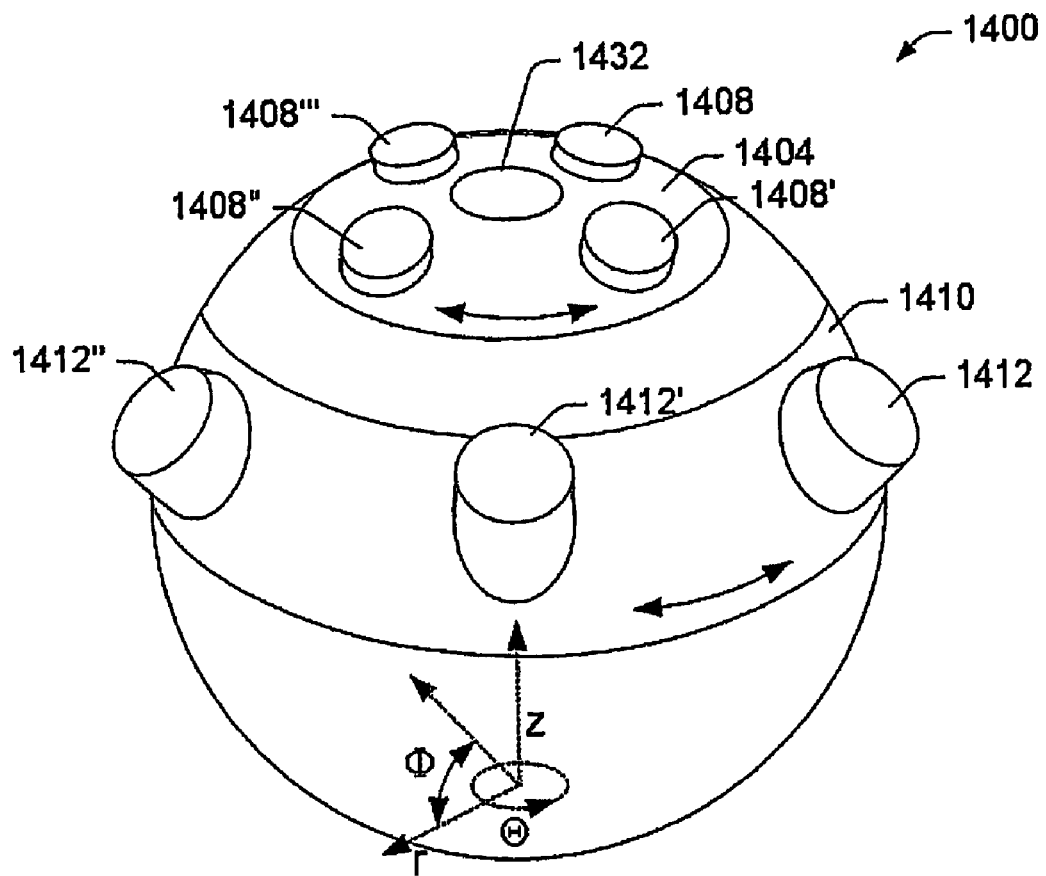
FIG. 14 is a perspective view diagram of another exemplary reflectometer chamber.

FIG. 14 shows yet another exemplary chamber 1400 having an exemplary arrangement of radiation sources. The exemplary chamber 1400 includes an upper rotatable section 1404 (e.g., rotatable in the azimuthal angle, Θ) that has a plurality of radiation sources 1408, 1408', 1408", 1408''' positioned thereon, referred to herein as $RS_3$ sources. Hence, rotation of the section 1404 may allow for improved illumination of a wafer having particular geometry. The plurality of radiation sources $RS_3$ are positioned substantially normal to the rAΘ-plane, where Θ is the azimuthal angle (e.g., at an altitudinal angle Φ equal to or greater than approximately 70°. These radiation sources are suitable for illuminating a wafer with radiation directed substantially normal to the wafer. While the exemplary chamber 1400 has four radiation sources 1408, 1408', 1408", 1408''', a lesser or greater number are optionally used. For example, an exemplary chamber optionally includes a single ring-shaped source positioned at or near an upper aperture 1432, two sources positioned at altitudinal angles (e.g., Φ) equal to or greater than approximately 70°, or 8 sources positioned at altitudinal angles (e.g., Φ) equal to or greater than approximately 70°, etc.

The exemplary chamber 1400 optionally includes an additional rotatable section 1410 having additional radiation sources 1412, 1412', 1412", etc., positioned at lesser altitudinal angles (e.g., Φ), referred to as $RS_2$ sources. Hence, rotation of the section 1410 may allow for improved illumination of a wafer having particular geometry. These additional sources $RS_2$ are suitable for illuminating wafers having substantial surface texture (e.g., roughness). Hence, the exemplary chamber 1400, as shown, is suitable for illuminating wafers having a wide variety of surface characteristics. A controller, such as the controller 1238, optionally controls radiation sources and may select or adjust illuminating radiation to account for such surface characteristic variations.

Figure 15:
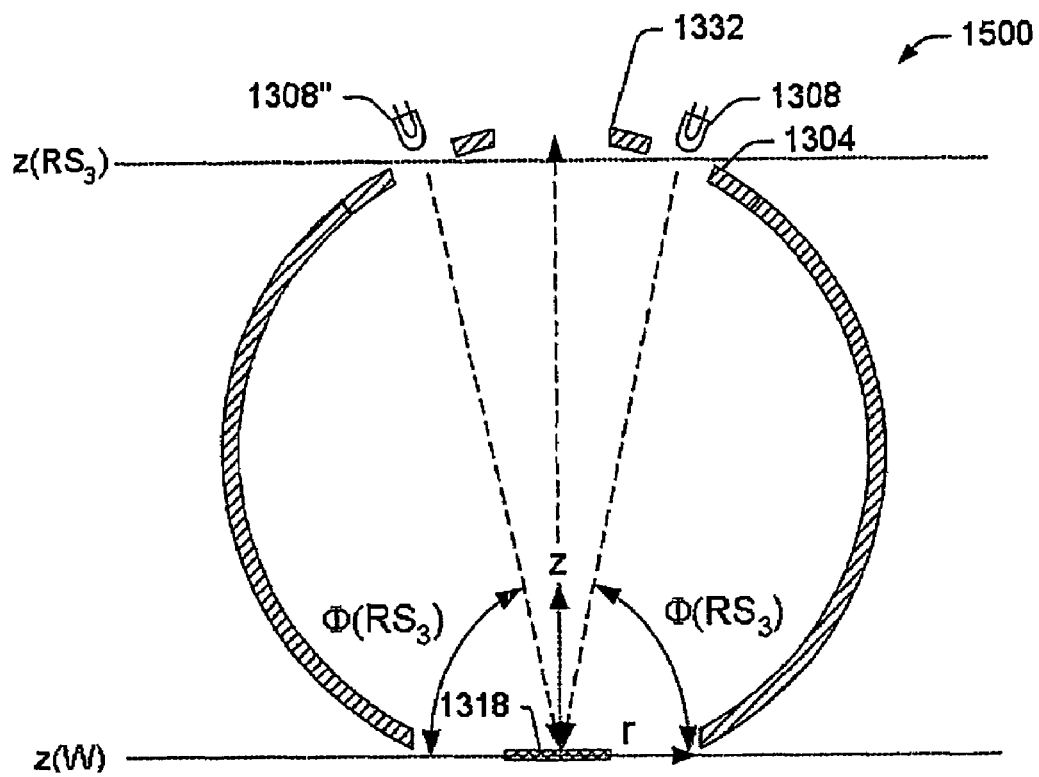
FIG. 15 is a cross-sectional view diagram of the exemplary chamber of FIG. 13.

FIG. 15 shows a cross-sectional view of the exemplary chamber 1300 of FIG. 13. This particular cross-section shows the section 1304, two of the radiation sources 1308, 1308", an upper aperture 1332 (e.g., defined by the section 1304) and a wafer 1318. The radiation sources 1308, 1308" are positioned at a distance $z=z(RS_3)$ and at an altitudinal angle $\Phi=\Phi(RS_3)$. Again, radiation from the sources 1308, 1308" can illuminate the wafer 1318 from a direction substantially normal to the wafer. Radiation reflected from the wafer 1318 is at least in part directed substantially normal to the wafer (e.g., along the z-axis) and through the upper aperture 1332 of the chamber 1300. The exemplary chamber 1300 is optionally suitable for use in measuring reflectance of wafers having little surface texture (e.g., one or more polished surfaces). In general, the term "polished" refers to a surface characteristic that may be achieved via any of a variety of processing techniques (e.g., including, but not limited to, polishing).

An exemplary method includes illuminating a wafer with radiation from one or more radiation sources positioned at a first altitudinal angle and then illuminating the wafer with radiation from one or more radiation sources positioned at a second altitudinal angle. Such an exemplary method can help in determining thickness and/or surface characteristics of a wafer.

Another exemplary method includes illuminating a wafer having substantial surface texture using one or more radiation sources positioned at a first altitudinal angle and illuminating another wafer having lesser surface texture (e.g., more polished, etc.) using one or more radiation sources positioned at a second altitudinal angle wherein the second altitudinal angle is greater than the first altitudinal angle.

Yet another exemplary method includes measuring reflectance of a wafer and then selecting one or more radiation sources from a group of radiation sources positioned at a plurality of altitudinal angle. Such an exemplary method may help to achieve a more accurate measurement of wafer thickness and/or surface characteristics.

Another exemplary method rotates a section of a chamber to position radiation sources with respect to geometry of a wafer. For example, a rectangular wafer may have a dominant axis (e.g., along a particular azimuthal angle Θ as defined above). In this example, rotation of a section may allow for positioning one or more radiation sources with respect to the dominant axis of the wafer.

Exemplary Element for Directing Reflected Radiation

Figure 16:
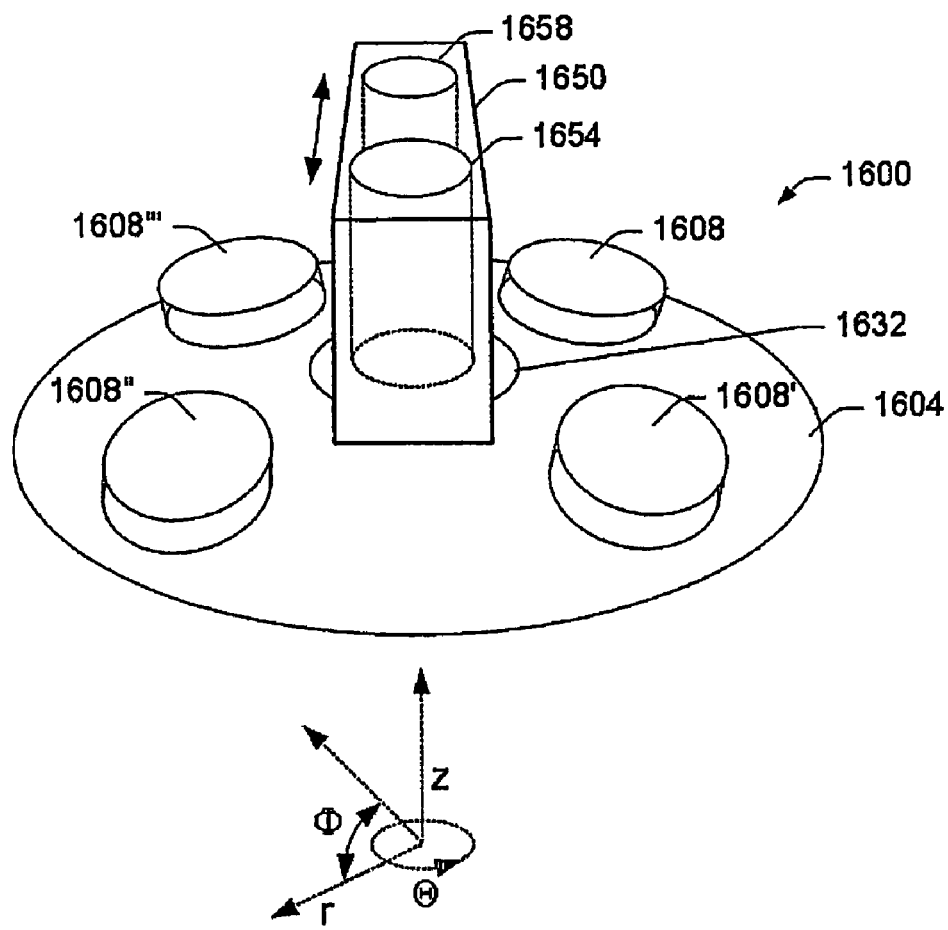
FIG. 16 is a perspective view diagram of an exemplary element and a component of an exemplary chamber.

FIG. 16 shows an exemplary system 1600 having an exemplary element 1650 for directing reflected radiation. For ease of description, the element 1650 is shown with respect to a section 1604 suitable for use as a part of a reflectometry chamber. Of course, the element 1650 is suitable for use with any of a variety of reflectometry chambers (e.g., chamber 1204, chamber 1300, chamber 1400, etc.).

The element 1650 has predominantly rectangular cross-sections which define a plurality of cylindrical apertures including a fore aperture 1654 and an aft aperture 1658. The element 1650 is positionable with respect to the upper aperture 1632 of the section 1604. In particular, the element 1650 is positionable to allow for substantial alignment between the upper aperture 1632 and the fore or aft apertures 1654, 1658. Any of a variety of positioning means may allow for positioning of the element 1650 in such a manner. For example, a sliding mechanism may allow the element 1650 to slide forward and backward thereby allowing for alignment of fore or aft apertures 1654, 1658 and the upper aperture 1632.

An exemplary element includes a first cylindrical aperture to receive a fiber capable of coupling radiation to a detector or analyzer and a second cylindrical aperture to transmit radiation to an imager (e.g., a camera).

Figure 17:
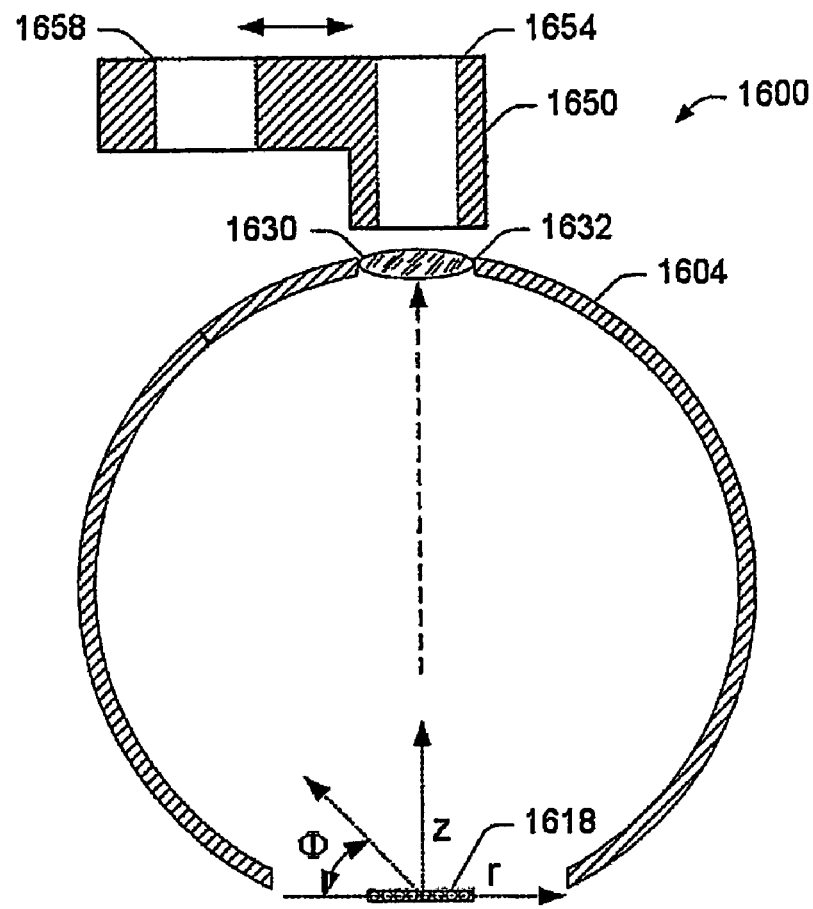
FIG. 17 is a cross-sectional view diagram of the exemplary element of FIG. 16.

FIG. 17 shows a cross-sectional view of the exemplary system 1600 of FIG. 16 and a wafer 1618 positioned in a chamber that has an optical element 1630 set in the upper aperture 1632. In this example, the fore aperture 1654 has a length greater than that of the aft aperture 1658. This arrangement allows for positioning a fiber close to the optical element 1630, which can increase coupling of radiation from the chamber to the fiber.

Figure 18:
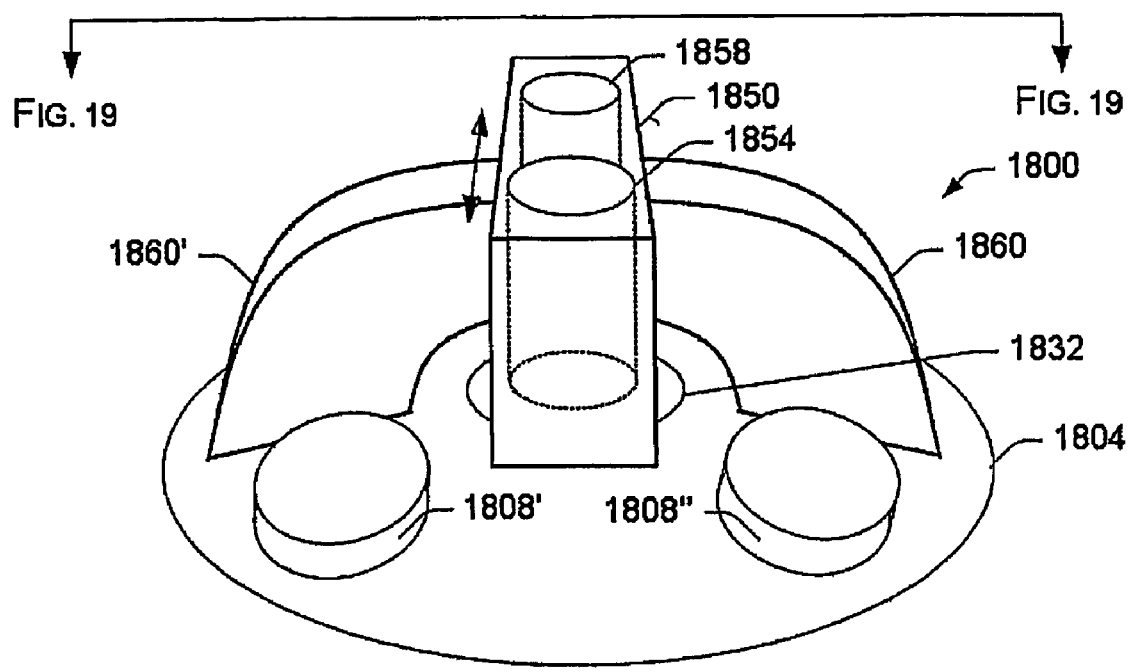
FIG. 18 is a perspective view diagram of an exemplary element, a positioning mechanism and a component of an exemplary chamber.
Figure 18:
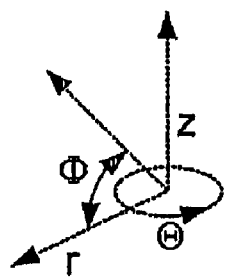

FIG. 18 shows an exemplary system 1800 having an element 1850 for directing reflected radiation. For ease of description, the element 1850 is shown with respect to a section 1804 suitable for use as a part of a reflectometry chamber. Of course, the element 1850 is suitable for use with any of a variety of reflectometry chambers (e.g., chamber 1204, chamber 1300, chamber 1400, etc.).

The element 1850 has predominantly rectangular cross-sections which define a plurality of cylindrical apertures including a fore aperture 1854 and an aft aperture 1858. The element 1850 is positionable with respect to the upper aperture 1832 of the section 1804. In particular, the element 1850 is positionable to allow for substantial alignment between the upper aperture 1832 and the fore or aft apertures 1854, 1858. Any of a variety of positioning means may allow for positioning of the element 1850 in such a manner. In the exemplary system 1800, a pair of arms 1860, 1860' extend from the section 1804 to respective sides of the element 1850. In this example, the arms 1860, 1860' allow the element 1850 to slide back and forth with respect to the section 1804 and hence allow for alignment of the fore or aft apertures 1854, 1858 and the upper aperture 1832.

Figure 19:
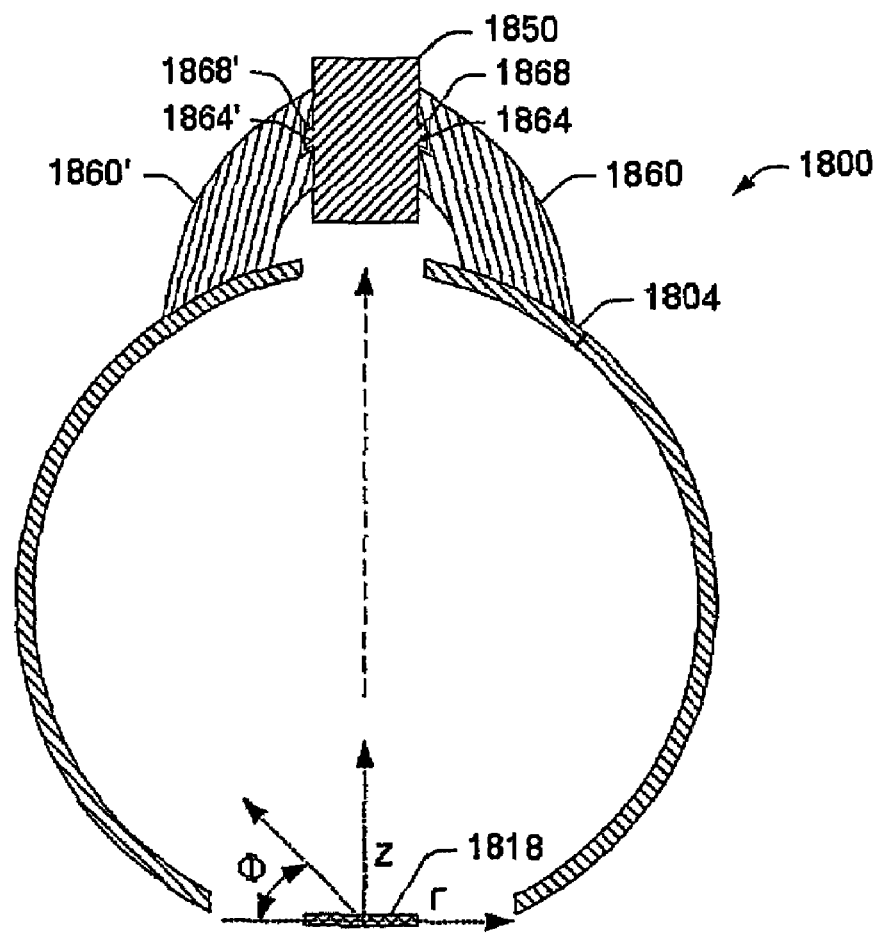
FIG. 19 is a cross-sectional view diagram of the element of FIG. 18.

FIG. 19 shows a cross-sectional view of the exemplary system 1800 along with a wafer 1818 positioned in a chamber. In the exemplary system 1800, the arms 1860, 1860' extend from the chamber section 1804 to respective sides of the element 1850. In this example, the arms 1860, 1860' allow the element 1850 to slide back and forth with respect to the section 1804 and hence allow for alignment of the fore or aft apertures 1854, 1858 and the upper aperture 1832. More specifically, in this example, the element 1850 has two rails 1864, 1864' and each arm 1860, 1860' has a groove 1868, 1868' capable of slidably receiving a respective rail 1864, 1864'. Accordingly, the element 1850 is positionable with respect to the upper aperture 1832 of a chamber or section (e.g., section 1804) thereof. Of course, a locking mechanism (e.g., screw, clamp, etc.) or a fine adjustment mechanism (e.g., micrometer type mechanism, etc.) may accompany such an exemplary system.

Exemplary Methods, Devices and/or Systems for Measuring

As previously noted, various industries, such as the solar cell industry, may use substrates that are formed from ribbons. For example, substrates may be formed or cut from silicon ribbons. Often these silicon ribbons are grown in the form of hollow octagons (other polygonal shapes may be possible as well). Such a hollow octagon may be formed from very thin single crystal silicon, for example, having a thickness of approximately 300 microns. Due to fragile nature of these ribbons, typical substrate cutting techniques, such as wire sawing, are unsuitable.

One method that is suitable to cutting such ribbons is laser cutting. However, while laser cutting has been used for cutting or otherwise preparing ribbon substrates, there are some issues associated with laser cutting that can limit the cutting speed and yield. For example, laser cutting involves local melting which can necessitate melt removal before melt hardening (e.g., melt freezing). Often, an air-jet is used to blow off melt prior to hardening. Laser cutting may also be sensitive to thickness. As discussed above, substrates can have significant thickness variations. Thus, an optimal system will adjust one or more laser cutting parameters (e.g., cutting speed, power, energy delivered, etc.) in response such variations in thickness.

As discussed herein, issues associated with laser cutting may be mitigated and/or controlled via an exemplary measuring device that relies on reflectance, as described above. In one example, the measuring device aids in determining thickness, which, in turn, is used to adjust one or more laser cutting parameters. Other uses, systems, etc., are also possible, some of which are described further below.

Figure 20:
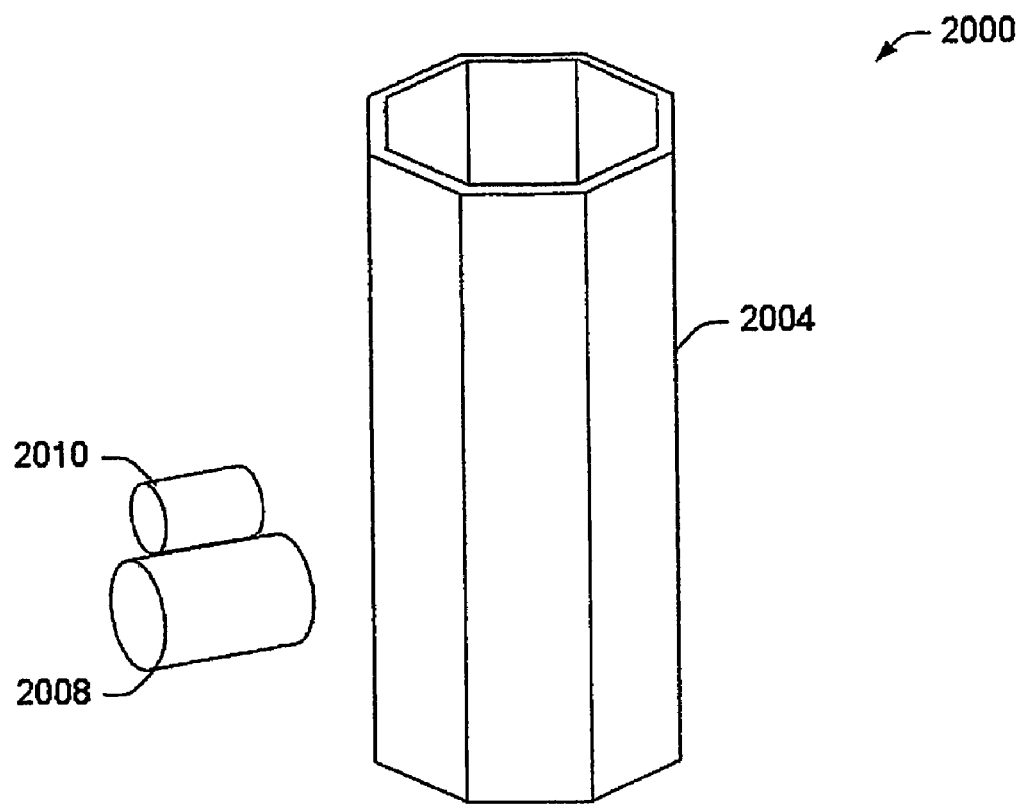
FIG. 20 is a perspective view of an exemplary system that includes a tubular or octagonal substrate, a cutting device and an exemplary substrate measuring device.

FIG. 20 shows an exemplary system 2000 that includes a substrate 2004, a cutting laser device 2008 and an exemplary measuring device 2010. To perform cutting, the laser device 2008 may move with respect to the substrate 2004, the substrate 2004 may move with respect to the laser device 2008, or the laser device 2008 and the substrate 2004 may move with respect to each other. As shown, the measuring device 2010 is associated with the laser device 2008 and hence has movement corresponding to the laser device 2008, if any. Further, the laser device 2008 may include an associated nozzle for directing pressurized gas such as air toward the substrate 2004.

The system 2000 may include local measurement of thickness using a non-contact optical method that is compatible with laser cutting speed (e.g., approximately 2.5 cm/s to approximately 10 cm/s). Thus, for wafers having dimensions of approximately 10 cm by 10 cm, a laser may make a suitable cut in approximately 1 second to approximately 4 seconds. Further, the method may include options that minimize interference from floating debris, laser light (e.g., YAG, 1.06 micron wavelength, etc.) and/or other conditions associated with laser cutting.

The exemplary measuring device 2010 typically precedes the cutting laser of the laser device 2008 or otherwise allows for a measurement that precedes a region to be cut by the laser device 2008. Information from the measuring device 2010 is then used to adjust laser power, laser speed, etc.

Thus, the system 2000 may include local measurement of thickness using a non-contact optical method wherein thickness measurement is used to determine a laser cutting speed and/or laser cutting power. For example, if an exemplary reflectometer indicates that thickness of a substrate is increasing along a prospective cut, then the laser cutting speed may be decreased and/or the laser cutting power increased, as appropriate. Similarly, if an exemplary reflectometer indicates that thickness of a substrate is decreasing along a prospective cut, then the laser cutting speed may be increased and/or the laser cutting power decreased. Consequently, power may be conserved, cutting time decreased, quality of cut maintained, etc., through optimizations based on such thickness measurements. Cutting may also involve rotational movement of a laser and/or substrate.

As described above, reflectance spectroscopy may be used to determine thickness and/or other characteristics of a substrate. An exemplary measuring device (e.g., the device 2010) optionally uses a selected band of reflectance to determine thickness of a substrate wherein one or more surface characteristics of the substrate are known. With respect to selection of a band, wavelength(s) may be selected via filtering, a narrow-band emission source, etc. As described herein, total reflectance may be used to determine local absorption, which is then used to determine local thickness of a substrate.

While FIG. 20 references a cutting process, the exemplary reflectometer may be used in crystal growth or thin film deposition processes. For example, an exemplary reflectometer may measure characteristics of a thin film being deposited on a moving substrate where reflectometer measurements may control movement of the substrate, deposition parameters, quality, etc., via appropriate control logic. Crystal growth processes may be controlled similarly. For example, reflectometer measurements may provide one or more control logic parameters for a crystal growth process. In general, such control schemes can enhance quality and/or diminish cost.

Figure 21:
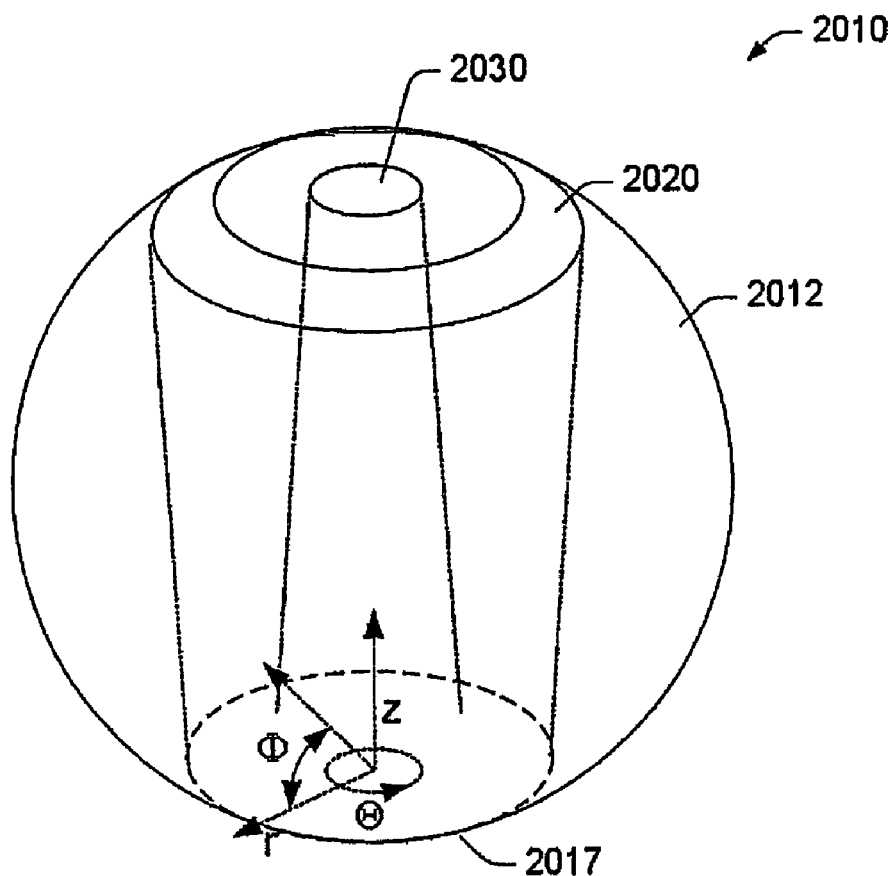
FIG. 21 is a perspective view of an exemplary reflectometry suitable for use as the substrate measuring device of FIG. 20.

FIG. 21 shows an exemplary reflectometer 2010 that includes a chamber 2012, a radiation source 2020 (e.g., light source) and a collector 2030. The chamber 2012 includes an aperture 2017. The substantially annular radiation source 2020 can direct radiation in the chamber 2012 to the aperture 2017 while the collector 2030 can collect reflected radiation that passes through the aperture 2017 and in to the chamber 2012. While various examples refer to a measuring device as a reflectometer, such measuring devices or reflectometers are typically components of a reflectometer or system (e.g., optionally electronics, software/hardware, etc.).

In the example of FIG. 21, the chamber 2012 has properties such as those discussed above. The radiation source 2020 is optionally a ring or annular radiation source that focuses radiation, either directly or indirectly, through an opening in the chamber 2012. The radiation is then reflected off the substrate (not shown), at least in part along the z-axis to the collector 2030, which then directs the radiation to a detector for analysis. In accordance with one implementation, the radiation source 2020 emits radiation provided to it from one or more optical fibers. The source 2020 may optionally include a plurality of "sources," for example, a ring may include a plurality of sources in a ring arrangement.

With respect to the collector 2030, in accordance with one implementation, a single Ge detector is used. The Ge detector is particularly useful in applications where the thickness of a silicon substrate is being measured. Other detectors may optionally include GaAs, mercury cadmium telluride (MCT), Si or other material.

A filter is optionally positioned with respect to the collector 2030 to collect only a selected narrow band of wavelengths. While other examples discussed above typically have more than one radiation source, the exemplary device 2000 optionally uses a single source.

Figure 22:
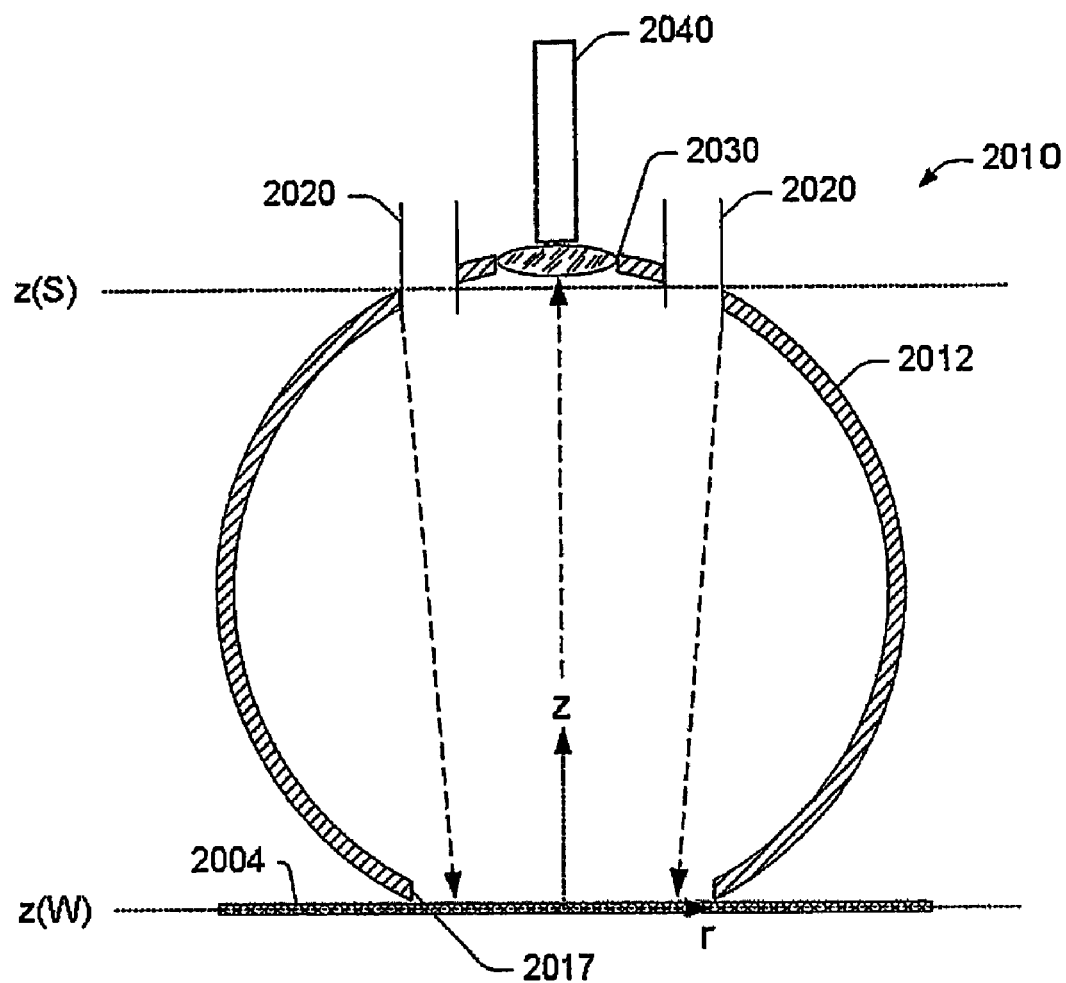
FIG. 22 is a cross-sectional view of the exemplary reflectometry of FIG. 21.

FIG. 22 shows a cross-sectional view of the exemplary reflectometer 2010. In this example, the exemplary reflectometer 2010 includes a lens at the collector 2030 and an optical fiber(s) or other structure 2040 for transmitting radiation from the collector 2030 to suitable electronics for analysis. Also shown in FIG. 22 is a substrate 2004 positioned at some position along the z-axis. While the substrate 2004 is shown proximate to the chamber 2012, the substrate may be positioned at any suitable distance wherein illumination and collection of reflected radiation are possible, e.g., via the aperture 2017.

Figure 23:
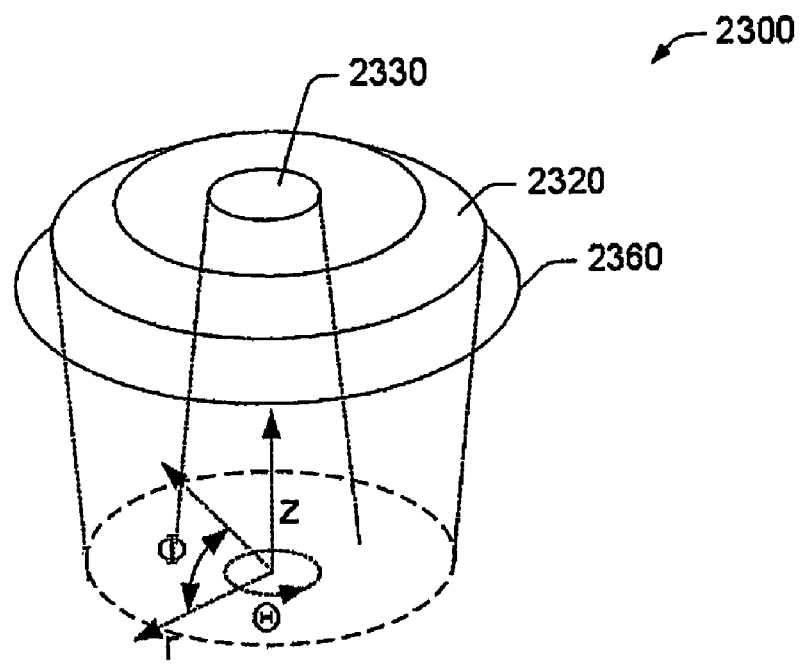
FIG. 23 is a perspective view of another exemplary measuring device suitable for use in the system of FIG. 20.

FIG. 23 shows another exemplary reflectometer 2300 for use in measuring thickness or other parameters to adjust and/or control a cutting process. In this example, the reflectometer 2300 includes a lens 2360, a radiation source 2320 and a collector 2330. The lens 2360 acts to direct radiation from the radiation source 2320 to the substrate and reflected radiation from the substrate to the collector 2330. In this example, the radiation source 2320 is a substantially annular radiation source and the lens 2360, radiation source 2320 and the collector 2330 are substantially aligned along a common axis (i.e., z-axis).

In general, such a reflectometer can measure the entire reflectance spectrum (e.g., using an optical fiber to transmit collected radiation to suitable electronics to generate a broad R versus λ spectrum, etc.). In some instances, an entire or a broad spectrum is not required to determine one or more parameters of thickness, related to thickness, etc. For example, if the surface quality of the substrate is known, then it is possible to generate a thickness value from reflectance in a suitably selected, narrow wavelength band. In such situations, the optical fiber and the electronics may be replaced with a filtered detector using, for example, a broadband radiation source. Alternatively, a radiation source itself may be chosen to emit a narrow-band, such as an LED or a laser diode. Additionally, combinations of bands may also be possible.

In some instances, a measuring device may be positioned close to the substrate, which can act to reduce sensitivity to changes in substrate surface characteristics, reduce size of the measuring device (and possibly mass), reduce sensitivity to ambient or stray radiation, and reduce at least some debris.

In some instances, a measuring device has a chamber provided with a positive pressure to avoid debris from entering the chamber. Other arrangements of exemplary measuring devices may allow for use of pressured air or gas to prolong life and/or improve measurement quality. In general, such pressurized air or gas may be provided from a source already used for blowing off melt. In some instances, a reflectometer may provide measurements for controlling a cutting process wherein such control reduces a need for melt removal.

Figure 24:
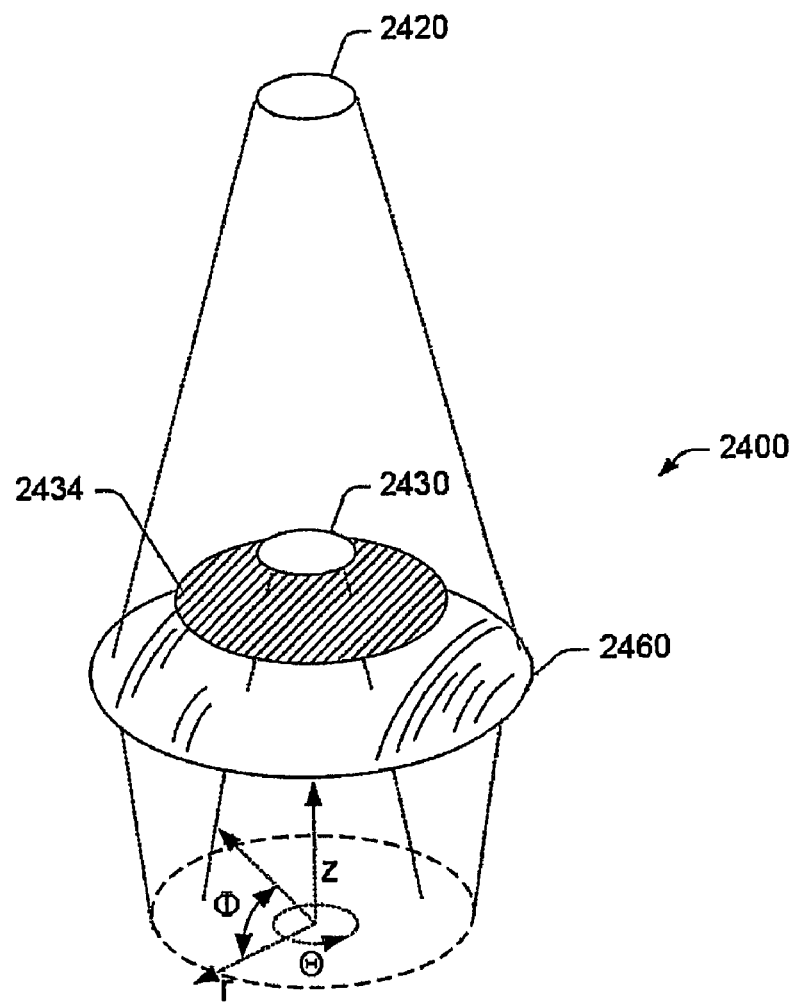
FIG. 24 is a perspective view of another exemplary measuring device suitable for use in the system of FIG. 20.

FIG. 24 shows another exemplary reflectometer 2400 wherein a radiation source 2420 is positioned above a collector 2430, which is positioned above a filter 2434. A lens 2460 directs radiation to and from a substrate. Various lines or paths shown in this example are illustrative of non-limiting examples wherein specific paths will depend on characteristics of the source 2420, the collector 2430, the filter 2434, the lens 2460, etc. The filter 2434 optionally acts to exclude stray radiation from reaching the collector 2430.

Figure 25:
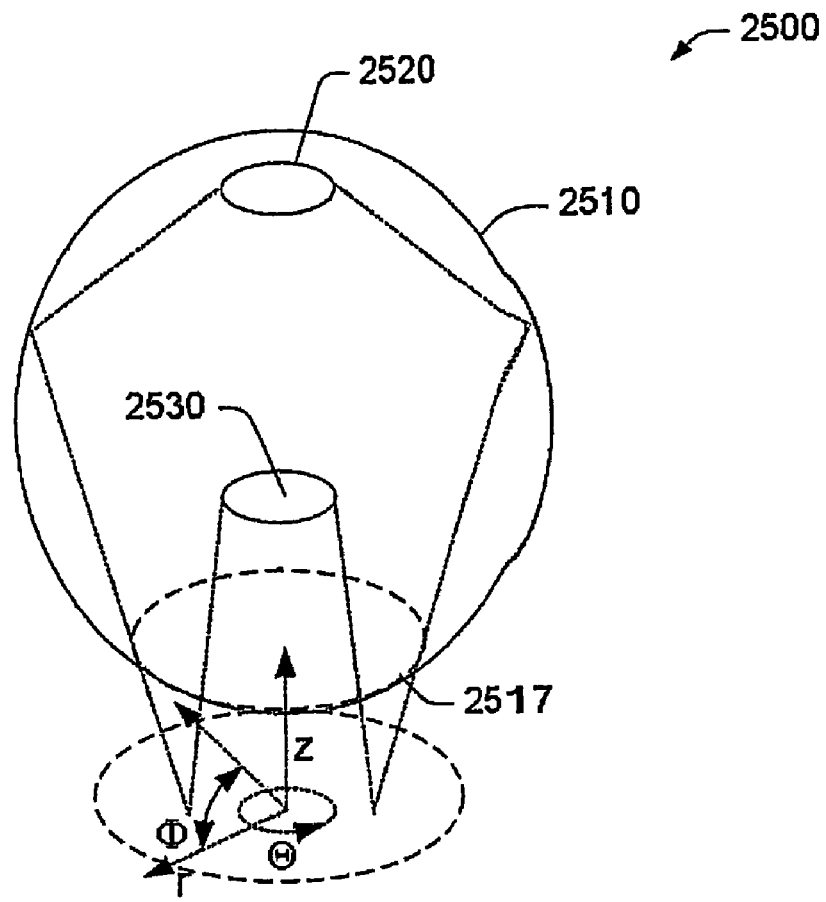
FIG. 25 is a perspective view of another exemplary measuring device suitable for use in the system of FIG. 20.

FIG. 25 shows an exemplary reflectometer 2500 that includes a chamber 2510 with an aperture 2517 (i.e., an opening), a radiation source 2520, and a collector 2530. In this example, the collector 2530 optionally includes a filter, such as the filter 2434 of the prior example. The chamber 2510 optionally has a shape other than spherical to promote at least some focusing of radiation emitted from the radiation source 2520 and through the aperture 2517. Thus, an exemplary reflectometer may include a walled chamber having a reflective inner wall surface and an aperture wherein the shape of the walled chamber acts to focus radiation from a radiation source through the aperture and a collector positioned in the chamber to collect radiation that passes through the aperture and into the chamber.

Again, as in various other examples, such a reflectometer or chamber may include a pressurized air or gas connection to reduce risk of debris from entering the chamber. For example, the chamber 2510 may have, at times, a positive pressure that aims to prevent debris from entering the chamber 2510 via the aperture 2517.

While various exemplary measuring devices and/or components thereof are shown, other examples may rely on such components and/or devices in other arrangements. Further, exemplary methods for using such measuring devices and/or components thereof are included and either implicit or explicit based on the aforementioned examples. For instance, an exemplary method includes measuring thickness of a substrate using reflected radiation and adjusting one or more parameters related to a cutting process in response the measuring.

The invention claimed is:

1. A system comprising:
   a measuring device to acquire non-contact thickness measurements of a wafer wherein the measurements are based at least in part on changes in reflectance of radiation caused by wafer thickness related changes in absorbance of radiation by the wafer;
   a laser beam to cut the wafer at a rate based at least in part on one or more thicknesses measurements; and
   a source of pressurized air to reduce risk of interference by floating wafer cutting debris on the non-contact thickness measurements.

2. The system of claim 1 further comprising a laser that emits the laser beam.

3. The system of claim 2 wherein the measuring device and the laser comprise a moveable assembly.

4. The system of claim 1 wherein the rate corresponds to movement of at least one member selected from a group consisting of the laser beam and the wafer.

5. The system of claim 1 wherein the rate comprises a speed of at least 2.5 cm/s.

6. The system of claim 1 wherein the laser beam comprises a wavelength of approximately 1.06 micron.

7. The system of claim 1 wherein the rate depends on the power of the laser beam.

8. The system of claim 1 wherein the measuring device comprises a partially walled focusing chamber to direct radiation reflected from the wafer.

9. The system of claim 1 wherein the measuring device relies at least in part on total reflectance.

10. The system of claim 1 wherein the measuring device relies at least in part on a selected band of wavelengths.

11. The system of claim 1 wherein the wafer comprises silicon.

12. The system of claim 1 wherein the wafer comprises a hollow polygonal ribbon.

13. The system of claim 1 wherein the measuring device comprises a reflectometer.

14. The system of claim 13 wherein the reflectometer comprises a partially walled chamber, a radiation source and a collector.

15. The system of claim 1 wherein the measuring device comprises a partially walled chamber having a substantially spherical shape.

16. The system of claim 1 wherein the measuring device comprises a substantially annular radiation source.

17. The system of claim 1 wherein the measuring device comprises a detector that comprises geranium.

18. The system of claim 1 wherein the measuring device comprises a collector and a filter positioned to provide the collector with filtered radiation.

19. The system of claim 1 wherein the measuring device comprises a lens to direct radiation to a collector.

20. A method comprising:
   providing a substrate;
   illuminating the substrate with radiation;
   measuring at least some radiation reflected from the substrate;
   determining one or more cutting parameters based at least in part on the reflectance of the measured radiation in a selected wavelength band wherein a thickness related change in absorbance of radiation by the substrate changes the reflectance of the measured radiation;
   cutting the substrate using the one or more cutting parameters; and
   using pressurized air to reduce risk of interference by floating debris during the measuring of radiation reflected from the substrate.

21. An assembly comprising:
   a walled reflectometer chamber comprising a base opening that defines a horizon, one or more radiation sources positioned at an altitudinal angle equal to or greater than approximately 70° from the horizon to emit radiation to the base opening and one or more additional radiation sources positioned at an altitudinal angle less tan approximately 70° from the horizon to emit radiation to the base opening wherein the radiation sources provide for illuminating wafers having a wide variety of surface characteristics in at least a moderately absorbing band of wavelengths; and
   a laser that emits a laser beam capable of cutting a wafer at a rate wherein the rate is based at least in part on radiation from the radiation sources being reflected from the wafer.

22. The assembly of claim 21 wherein the rate comprises a speed.

23. The assembly of claim 22 wherein the speed corresponds to movement of at least
   one member selected from a group consisting of the laser beam and the wafer.

24. An assembly comprising:
   a walled reflectometer chamber comprising a base opening that defines a horizon, one or more radiation sources positioned at an altitudinal angle equal to or greater than approximately 70° from the horizon to emit radiation to the base opening and an inlet for air to provide the chamber with a positive pressure to avoid debris from entering the chamber; and
   a laser that emits a laser beam capable of cutting a wafer wherein power of the laser beam is based at least in part on radiation from the one or more radiation sources being reflected from the wafer.

25. The assembly of claim 24 wherein movement of the wafer or the laser beam occurs during cutting.

26. The assembly of claim 24 wherein the movement is based at least in part on radiation from the one or more radiation sources being reflected from the wafer.

27. A reflectometer comprising:
   a walled chamber having an aperture;
   a substantially annular radiation source to direct radiation in the chamber and to the aperture;
   a collector to collect reflected radiation that passes in to the chamber via the aperture; and
   a source of pressurized air to provide the chamber with a positive pressure to prevent floating debris from entering the chamber.

28. The reflectometer of claim 27 wherein the aperture, the substantially annular radiation source and the collector are substantially aligned along a common axis.

29. The reflectometer of claim 27 wherein a substrate reflects radiation in to the chamber via the aperture and wherein radiation collected by the collector allows for determination of thickness of the substrate.

30. A reflectometer comprising:
   a lens;
   a substantially annular radiation source; and
   a collector wherein the lens directs radiation emitted by the substantially annular radiation source to a substrate and reflected radiation from the substrate to the collector.

31. The reflectometer of claim 30 wherein the lens, the substantially annular radiation source and the collector are substantially aligned along a common axis.

32. The reflectometer of claim 30 wherein radiation collected by the collector allows for determination of thickness of the substrate.

33. A reflectometer comprising:
a broadband radiation source;
a collector;
a narrow band filter wherein the narrow band corresponds at least in part to a moderately absorbing region of a substrate; and
a lens to direct radiation emitted by the broadband radiation source to a substrate, wherein at least some of the broadband radiation bypasses the filter, and to direct reflected radiation from the substrate through the narrow band filter and to the collector.

34. The reflectometer of claim 33 wherein radiation collected by the collector allows for determination of thickness of the substrate.

35. The reflectometer of claim 33 wherein the lens, the filter, the collector and the radiation source are substantially aligned along a common axis.

36. A reflectometer comprising:
a walled chamber having a reflective inner wall surface and an aperture wherein the walled chamber has a shape that acts to reflect and focus radiation from a radiation source through the aperture; and
a collector positioned in the chamber below the source and above the aperture to collect radiation that passes through the aperture and into the chamber.

* * * * *